US008303577B2

(12) United States Patent
Dick et al.

(10) Patent No.: US 8,303,577 B2
(45) Date of Patent: Nov. 6, 2012

(54) METHOD DEVICE AND SYSTEM FOR DETERMINING A SYSTEM PARAMETER OF A LASER BEAM TREATMENT SYSTEM

(75) Inventors: Manfred Dick, Gefell (DE); Hartmut Vogelsang, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 960 days.

(21) Appl. No.: 10/565,511

(22) PCT Filed: Jul. 13, 2004

(86) PCT No.: PCT/EP2004/007733
§ 371 (c)(1),
(2), (4) Date: Jan. 14, 2008

(87) PCT Pub. No.: WO2005/011544
PCT Pub. Date: Feb. 10, 2005

(65) Prior Publication Data
US 2011/0276042 A1   Nov. 10, 2011

(30) Foreign Application Priority Data

Jul. 23, 2003  (DE) .................................. 103 33 562

(51) Int. Cl.
*A61F 9/01* (2006.01)

(52) U.S. Cl. .............................................. 606/5; 606/11

(58) Field of Classification Search ................... 128/898; 606/4–6
See application file for complete search history.

(56) References Cited

U.S. PATENT DOCUMENTS

| 4,669,466 A * | 6/1987 | L'Esperance ..................... 606/3 |
| 5,261,822 A | 11/1993 | Hall et al. |
| 5,349,440 A | 9/1994 | DeGroot |
| 5,460,627 A * | 10/1995 | O'Donnell, Jr. .................. 606/4 |
| 5,520,679 A * | 5/1996 | Lin .................................. 606/5 |
| RE37,504 E * | 1/2002 | Lin .................................. 606/5 |
| 6,369,898 B1 * | 4/2002 | Van Saarloos et al. ....... 356/497 |
| 6,572,230 B2 * | 6/2003 | Levine .......................... 351/221 |
| 6,616,275 B1 | 9/2003 | Dick et al. |
| 6,702,806 B2 * | 3/2004 | Gray et al. ....................... 606/5 |
| 2002/0026181 A1 * | 2/2002 | O'Donnell, Jr. ................ 606/10 |
| 2003/0149426 A1 * | 8/2003 | Yee et al. ......................... 606/5 |
| 2003/0225399 A1 * | 12/2003 | Chernyak et al. ................ 606/5 |

FOREIGN PATENT DOCUMENTS

| DE | 198 41 176 A1 | 3/2000 |
| DE | 100 24 080 A1 | 11/2001 |
| EP | 0 372 127 A1 | 6/1990 |
| EP | 1 231 496 A2 | 8/2002 |
| WO | WO 96/30082 | 10/1996 |
| WO | WO 99/04220 | 1/1999 |
| WO | WO 03/101355 A1 | 12/2003 |

* cited by examiner

*Primary Examiner* — Henry M Johnson, III
(74) *Attorney, Agent, or Firm* — Patterson Thuente Christensen Pedersen, P.A.

(57) ABSTRACT

The invention relates to a method for determining an actual value of at least one system parameter or a deviation from a set value of at least one parameter of a system for the treatment of an eye using a treatment laser beam emitted by said system. According to the invention, the surface of a calibrating body is ablated with at least a partial beam of the treatment laser beam with a predetermined ablation program. The surface ablated by the treatment laser beam is examined by means of aberrometry and/or profilometry. The actual value of the system parameter or the deviation from the set value of the system parameter is determined on the basis of the examination data detected during the examination.

36 Claims, 8 Drawing Sheets

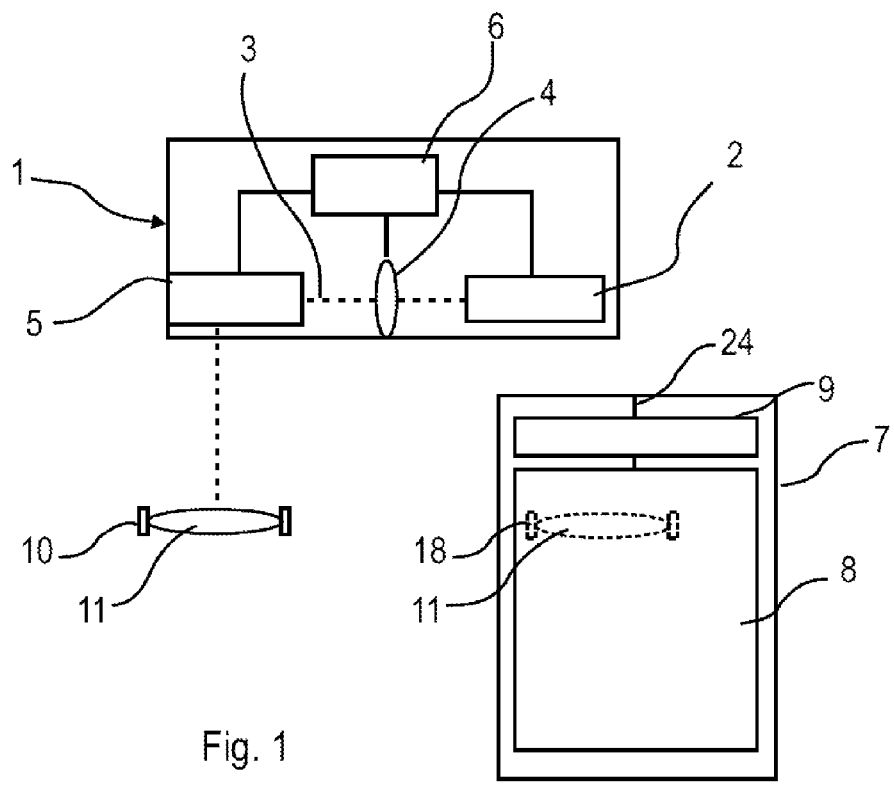
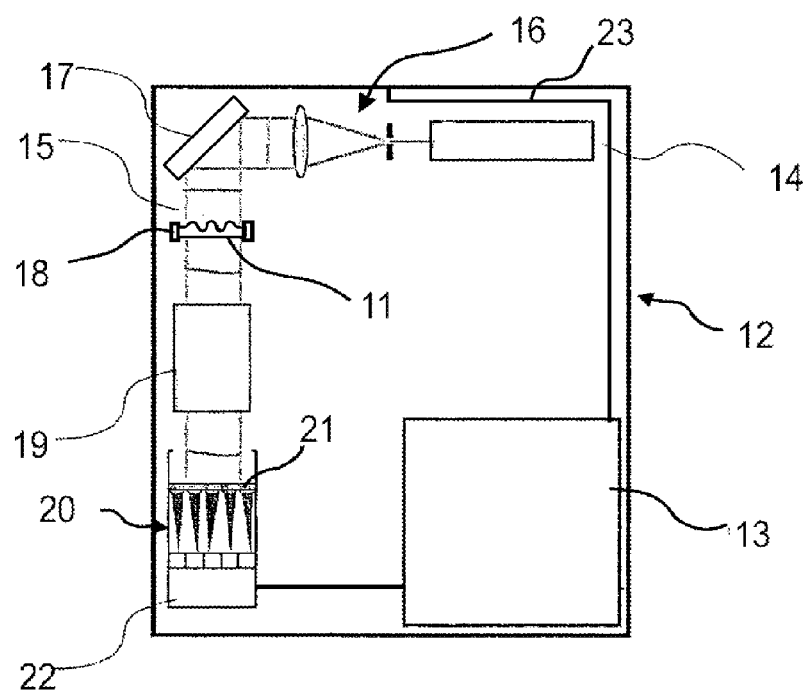
Fig. 1
Fig. 2

| 1 | 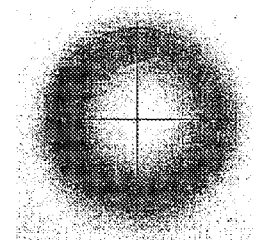 | Z3-3 = 2<br>Z3-1 = 125<br>Z31 = -25<br>Z33 = -51<br>Z4-4 = -31<br>Z4-2 = -12<br>Z 40 = 1211<br>Z42 = 85<br>Z44 = -84 |
|---|---|---|
| 2 | 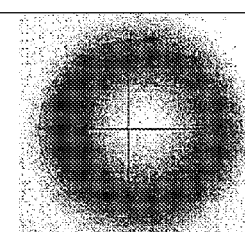 | Z3-3 = -16<br>Z3-1 = -1120<br>Z31 = -132<br>Z33 = -41<br>Z4-4 = -28<br>Z4-2 = -12<br>Z 40 = 1252<br>Z42 = 23<br>Z44 = -19 |
| 3 | 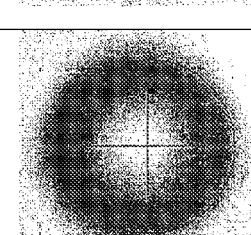 | Z3-3 = 83<br>Z3-1 = 1125<br>Z31 = -34<br>Z33 = -61<br>Z4-4 = 2<br>Z4-2 = -51<br>Z 40 = 1170<br>Z42 = 112<br>Z44 = -83 |
| 4 | 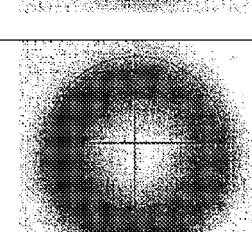 | Z3-3 = -47<br>Z3-1 = 0<br>Z31 = 1179<br>Z33 = -60<br>Z4-4 = -58<br>Z4-2 = -48<br>Z 40 = 1175<br>Z42 = 44<br>Z44 = -58 |
| 5 | 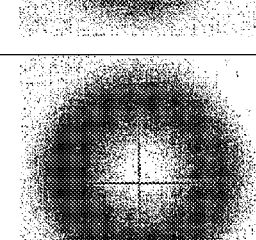 | Z3-3 = 4<br>Z3-1 = 109<br>Z31 = -1110<br>Z33 = -25<br>Z4-4 = 9<br>Z4-2 = 8<br>Z 40 = 1179<br>Z42 = 24<br>Z44 = -114 |
Fig. 5

| | | | |
|---|---|---|---|
| 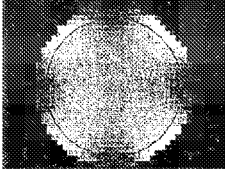 |  | 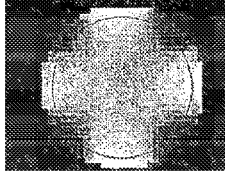 | 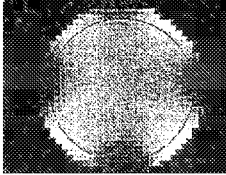 |
| Z(4;-4) = 0.039 µm<br>Z(4;-2) = -0.003 µm<br>Z(4;0) = -0.076 µm<br>Z(4;2) = -0.024 µm<br>Z(4;4) = -1.099 µm | Z(4;-4) = -1.093 µm<br>Z(4;-2) = -0.004 µm<br>Z(4;0) = -0.085 µm<br>Z(4;2) = -0.009 µm<br>Z(4;4) = 0.026 µm | Z(4;-4) = -0.074 µm<br>Z(4;-2) = 0.001 µm<br>Z(4;0) = -0.088 µm<br>Z(4;2) = 0.013 µm<br>Z(4;4) = 1.083 µm | Z(4;-4) = 0.014 µm<br>Z(4;-2) = 0.032 µm<br>Z(4;0) = -0.091 µm<br>Z(4;2) = 0.019 µm<br>Z(4;4) = -1.039 µm |
| 0° | 22.5° | 45° | 90° |

Fig. 6

| | |
|---|---|
| 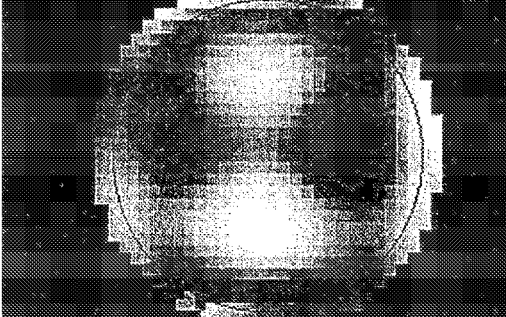 | Z(4;0) = 0,104 µm   Z(5;5) = 0.055 µm<br>Z(4;2) = -0.265 µm   Z(6;-6) = 0.052 µm<br>Z(4;4) = 0.136 µm   Z(6;-4) = 0.010 µm<br>Z(5;-5) = -0.031 µm   Z(6;-2) = 0.011 µm<br>Z(5;-3) = 0.001 µm   Z(6;0) = 0.125 µm<br>Z(5;-1) = -0.075 µm   Z(6;2) = 0.455 µm<br>Z(5;1) = 0.018 µm   Z(6;4) = 0.082 µm<br>Z(5;3) = 0.016 µm   Z(6;6) = 0.121 µm |
| 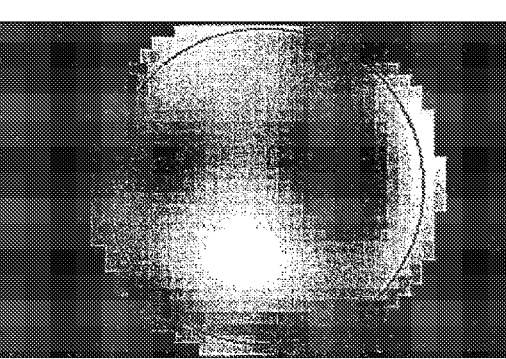 | Z(4;0) = -0.010 µm   Z(5;5) = 0.001 µm<br>Z(4;2) = -0.118 µm   Z(6;-6) = 0.030 µm<br>Z(4;4) = 0.023 µm   Z(6;-4) = -0.009 µm<br>Z(5;-5) = -0.045 µm   Z(6;-2) = 0.034 µm<br>Z(5;-3) = -0.006 µm   Z(6;0) = -0.014 µm<br>Z(5;-1) = -0.069 µm   Z(6;2) = 0.141 µm<br>Z(5;1) = -0.065 µm   Z(6;4) = 0.032 µm<br>Z(5;3) = -0.012 µm   Z(6;6) = 0.034 µm |

Fig. 7

METHOD DEVICE AND SYSTEM FOR DETERMINING A SYSTEM PARAMETER OF A LASER BEAM TREATMENT SYSTEM

FIELD OF THE INVENTION

The invention relates to a method of determining actual values and/or deviations from desired values of at least one system parameter of a treatment system for treatment of an eye with a laser beam and to means for carrying out said method.

BACKGROUND

Laser surgery on the cornea of the human eye is an established method of treating visual defects caused by deviations in the shape of the cornea of the eye from the ideal shape. This involves removal, e.g. by ablation, of material from the cornea using a treatment laser, such as an excimer laser, for example.

In order to carry out the treatment, use can be made, in particular, of so-called spot scanning systems, wherein a treatment laser beam of the treatment system or the corresponding treatment laser beam spot, respectively, is moved over the cornea by means of a deflecting unit, also referred to as a scanning unit, according to a predetermined ablation program, and causes an ablation at predetermined locations. The lasers of use are characterized primarily by a small effective spot diameter, which allows to ablate small areas on the cornea and, thus, to locally modify the refractive power of the cornea and of the eye.

This treatment method allows patient-specific corrections, also referred to as "customized ablation". These corrections comprise not only the sphero-cylindrical correction of visual defects, but also the correction of irregularities of the cornea, in particular also of spatially very small artifacts, and of higher aberrations, i.e. in particular also higher-order imaging errors characterized by high spatial frequencies, of the eye.

For treatment, first of all, the corneal topography is measured or the eye is examined, respectively, by means of aberrometers in order to detect irregularities or aberrations, respectively.

For the respective correction, ablation programs are then calculated, prior to surgery, by means of suitable programs, said ablation programs being based, inter alia, on empirical values for the ablation behavior of the cornea and defining the guidance and intensity of the treatment laser beam as a function of time. Using the treatment laser beam, which is emitted and guided according to the calculated ablation program, material is then ablated from the cornea.

The depths of removal in the cornea during correction of higher-order aberrations are usually only a fraction of the depths of removal required for correction of low-order refraction, in particular for sphero-cylindrical correction. Whereas sphero-cyiindricai corrections require a removal of about 12 μm per diopter on a 6 mm treatment pupil, in the correction of higher aberrations, the required local changes in power of refraction are achieved already by minor removal, i.e. generally already with one or few laser pulses.

Therefore, in sphero-cylindrical corrections, variations of system parameters of the treatment system, e.g. of the treatment laser parameters (such as, for example, the fluence of the laser), may average out statistically during ablation, so that a particularly exact adherence to the values of the system parameters is certainly desirable, but not critical. When correcting higher aberrations, however, a statistic compensation of variations in system parameters of the treatment system during ablation and, thus, smoothing of the ablation pattern on the cornea, may usually no longer be expected due to the low number of treatment laser pulses. The strict adherence to predetermined values of the system parameters is, therefore, critical for the correction of minimal details on the cornea and/or the treatment of visual defects which correspond to higher aberrations and are characterized by high spatial frequencies.

Therefore, on the apparatus-side, in addition to the standardization of the treatment atmosphere and the precision and speed of a system for tracking eye movements during treatment, which system may be, for example, a so-called "eye tracker", specifically also the stability and quality of calibration of the laser system and of the deflecting device are important for the quality of the treatment.

In order to adhere to the predetermined values of the system parameters, the treatment systems are suitably adjusted both at the factory and later, during maintenance. In essence, two methods are known for this purpose.

In the so-called fluence test, a predetermined test film is treated by the treatment system, which comprises a treatment laser, according to an ablation program specifically designed for said test, whereby a corresponding pattern forms on the film. Local breakthrough thresholds in the test film allow re-adjustment of the pulse energy of the treatment laser. On the one hand, this method allows to approximately determine the half width of the spot diameter of the treatment laser beam. On the other hand, control information on the quality of the scanner system of the treatment system may be obtained.

In another method, given sphero-cylindrical PMMA lenses can be ablated using an ablation program for sphero-cylindrical correction. The refractive power of the lenses thus obtained can be determined, e.g. by determining the focal length by means of a so-called lensometer, for example, with a precision of ca. 0.1 diopters and can be compared with an expected desired value for refractive power. For calibration, the pulse energy is then re-adjusted.

In known treatment methods, the pulse energy or fluence of the treatment laser is measured on-line during treatment, allowing a re-adjustment during the ablation procedure of said treatment in order to improve treatment successes.

However, said methods do not allow determination of further system parameters of the treatment system, which may have a considerable influence in view of the above-mentioned precision requirements, in particular those of a "customized ablation". Further, only indirect control of the ablation performance of the treatment system is obtained from the measurement of energy. The real progress of ablation during treatment cannot be measured, so that one has to rely on empirical values for re-adjustment. Therefore, fluctuations of the system parameters during treatment still limit the precision of treatment.

SUMMARY OF THE INVENTION

It is an object of the invention to provide a method allowing to determine an actual value of a system parameter or a deviation from a desired value of the system parameter of a system for treatment of an eye by laser radiation, as well as to provide a corresponding treatment device.

The object is achieved by a method for determining an actual value of at least one system parameter or a deviation from a desired value of at least one system parameter of an eye treatment system by means of a treatment laser beam emitted by said eye treatment system, wherein a surface of a calibrating body is ablated by at least one partial beam of the treatment laser beam according to a predetermined ablation program, the ablated surface is examined by means of aberrometry and/or profilometry, and the actual value of the system parameter or the deviation from the desired value of the system parameter is determined on the basis of examination data determined by said examination.

The object is further achieved by a system parameter determining device for determining at least one actual value of a system parameter or a deviation from a desired value of at least one system parameter of a system for treatment of an eye by means of a treatment laser beam emitted by said system, said device comprising a unit for examining at least one portion of an ablated surface of an ablated calibrating body by aberrometry and/or profilometry, and an evaluating unit connected to the examining unit, said evaluating unit determining the actual value of the system parameter or the deviation from the desired value of the system parameter on the basis of the examination data determined during examination.

An eye treatment system is understood to be a system comprising a treatment laser for emitting a treatment laser beam, a deflecting unit for deflecting the treatment laser beam, as well as a control unit which controls the emission and positioning of the treatment laser beam in space and time.

The object is further achieved by an eye treatment system, comprising a treatment laser for emission of a treatment laser beam, a deflecting unit for deflecting the treatment laser beam, a control unit which controls the emission and positioning of the treatment laser beam in space and time, a holder for a calibrating body onto which at least one partial beam of the treatment laser beam is directed for ablation, as well as a system parameter determining device according to the invention for determining at least one actual value or a deviation from a desired value of at least one system parameter of the eye treatment system.

The eye treatment system in the sense of the invention may be principally designed for any kind of eye treatments. However, the invention is particularly useful in treatment systems for ablative correction of the cornea of the eye.

A system parameter is understood to be any parameter describing the condition and/or function of the treatment system. In particular, physically directly detectable quantities and/or also empirically or operationally defined quantities may serve as system parameters.

Further, the system parameters may comprise parameters relating to properties of the treatment laser beam and parameters relating to the deflection of the treatment laser beam. The system parameters may concern, in particular, the physical condition of the treatment system, such as, for example, the adjustment of the treatment laser and/or the deflecting unit; the function, e.g. properties of the emitted laser beam, or even control parameters or a control program of the control unit.

If topography and/or aberrometry data, in particular wavefront data of the ablated calibrating body, are given as examination data, the system parameter is preferably selected from the group consisting of: centration and/or position of the deflecting unit relative to a system for tracking eye movements; the mean total fluence and/or energy and/or power of the treatment laser beam; the half-width of the treatment laser beam; information about the spot shape of the treatment laser beam; the energy distribution in the treatment spot, in particular hot spots therein; the characteristics of the transition zone between the optically active and inactive ablation zones and their relation to the beam parameters; the short-term and long-term stability of or fluctuations in total fluence and/or total energy and/or total power of the treatment laser beam; the short-term and long-term drift in the deflecting unit; the deviations from the optimal working distance, the efficiency of suction or removal of fumes generated by the ablated material during ablation; the temperature stability and the dependence of the system parameters on other ambient parameters. The system for tracking eye movements may be, in particular, an "eye tracker" or a limbus detector tracking the movements of capillaries in the eye.

According to the invention, the actual value of the system parameter or the deviation of the actual value from the desired value of the system parameter is not verified directly, but indirectly via the ablation of a calibrating body. The method is based, inter alia, on the fact that deviations of the actual values of certain system parameters result in certain characteristic changes in local optical properties, in particular in the topography or shape of the surface of the ablated calibrating body, said changes being detectable by means of aberrometry and/or profilometry. Actual values of the system parameters or deviations of the system parameters from a corresponding desired value may be determined from the examination data obtained by aberrometry and/or profilometry, i.e. aberrometric and/or topographical data, e.g. by using known relationships between system parameters and ablation profiles.

The influence (also in combination) of the above-mentioned system parameters on the ablation profile achieved is known. As examples, the depth of ablation as a function of the laser fluence, or the shape and depth of the transition zone, or the deviations in shape of certain higher aberrations generated in the calibrating body as a function of the spot shape, should be mentioned.

Prior to ablation, the calibrating body has a precisely determined surface, which is suitable for carrying out the method, and a predetermined ablation behavior at least in the region of possible ablations. The optical properties of the calibrating body are preferably selected according to the examination method used to examine the surface. For example, when using aberrometers, the calibrating body may be transparent for the optical radiation used in the aberrometer; in contrast thereto, the calibrating body is preferably absorptive or reflective when certain methods of profilometry are used.

The calibrating body, illuminated by at least a partial beam of the treatment laser beam, is held in the holder for the calibrating body during ablation using the treatment laser beam or the partial beam thereof. If necessary, the calibrating body may be mounted in a mount that can be placed, in a mechanically precise and reproducible manner, in the holder and, thus, in the beam path of the treatment laser beam or of the partial beam. As an alternative or in addition, the system parameter determining device according to the invention, too, may comprise a holder for the calibrating body, in which holder the calibrating body is held during ablation. The system parameter determining device is then usable in any desired treatment systems.

In order to verify the system parameter, a predetermined ablation pattern is ablated on the calibrating body according to a predetermined ablation program for given system parameters of the eye treatment system.

Ablation can be effected using the treatment laser beam or only a partial beam of the treatment laser beam. If the partial beam is used, it should be ensured, of course, that it is known how the properties of the partial beam depend on those of the treatment laser beam. This may be achieved, for example, by a suitable beam splitter.

Depending on the material of the calibrating body, ablation may cause not only a change in the shape of the calibrating body, but also local changes in the refractive index, due to laser-induced changes in the material of the calibrating body.

In order to achieve a predetermined ablation pattern on the calibrating body or on the eye, the treatment laser beam is controlled according to an ablation program, i.e. a predetermined temporal and local intensity profile of the treatment laser beam on the calibrating body or on the eye, respectively.

On the one hand, the ablation program or the predetermined ablation pattern may be an ablation program or pattern, which is intended only for examination and is calculated on the basis of specially determined, theoretical and/or real aberration and/or topography and/or wavefront data, and which allows particularly good examination and evaluation of the data obtained by aberrometry or profilometry, e.g. topographical data and/or wavefront data, in particular with simultaneous examination relating to various system parameters at the same time. The ablation pattern may comprise any desired surface profiles, e.g. a sphere, a cylinder, individual spots with a predetermined geometrical arrangement, series of excimer laser spots with a predetermined geometrical arrangement, or higher-order aberrations. In particular, it is preferred to design the ablation program so as to generate a surface profile on the calibrating body during ablation, which profile shows higher-order aberrations, i.e. aberrations having high spatial frequencies, when examined by optical aberrometry or by profilometry.

However, use may also be made of an ablation program provided for treatment, so that, immediately prior to surgery, the quality achievable on the basis of the actual condition of the laser system can be verified and, if necessary, re-adjusted or can be used to adjust the ablation profiles.

At least part of the ablated surface of the ablated calibrating body is then examined by means of aberrometry and/or profilometry. To this end, the system parameter determining device according to the invention is provided with the examining unit, which may comprise, in particular, an aberrometer and/or a profilometer.

The aberrometry of the calibrating body is understood to be, in particular, the sensing, e.g. by means of an aberrometer, of the deflection of rays or beams, as they pass through the calibrating body, as a function of the location of their passage or of the local deflection of a wavefront passing through the calibrating body. Since, in addition to a change in the shape of the calibrating body, a change in the local refractive index may principally occur as well, depending on the material used for the calibrating body, by a laser-induced change in material parameters, such changes are preferably also detected by said examination.

Profilometry is understood to be any method allowing the surface profile of the ablated calibrating body to be sensed at least in part of the ablated surface. As profilometers, in particular, topography systems can be used.

The examining unit may further comprise, in particular, a measurement data processing unit by means of which the acquired data can be evaluated. The measurement data processing unit may be provided, depending on the application, as a unit of the aberrometer or profilometer, separate from the treatment system and combined with a measurement data acquisition unit, or may be integrated into the treatment system. For example, the measurement data processing unit for an aberrometer reconstructs the wavefront from the acquired wavefront measurement data.

The actual value of the system parameter or a deviation from the desired value is then determined from the examination data. For this purpose, the examining unit is linked with an evaluating unit via a corresponding data link.

When determining at least one actual value of a system parameter, data are obtained which precisely define the instantaneous condition of the system and thus enable simple correction of the treatment system. In determining the deviation, it basically suffices that the deviation exceed a predetermined threshold value, but preferably, said deviation is also quantitatively determined.

In order to effect determination of the actual value or in order to determine said deviations, the evaluating unit may, in particular, comprise a data processing unit which is programmed to carry out the method. The evaluating unit may be a separate unit or may be integrated into the examining unit or into the treatment system.

An advantage over conventional methods is that, for the first time, the examination of the calibrating body by means of three-dimensional methods having high spatial resolution, namely aberrometry and profilometry, allows the three-dimensional ablation behavior to be detected not only integrally, but with a high lateral resolution. Only this allows also small and sensitive perturbations of the values of the system parameters to be detected, which would otherwise go unnoticed in an integral measurement, e.g. of fluence.

The examination of calibrating bodies, whose ablated surfaces cause, for example, higher aberrations and/or high spatial frequencies in optical imaging, by means of aberrometry and/or profilometry is considerably more sensitive to deviations of spot shape, spot size, or drift in the deflecting unit from corresponding desired values than the examination of the refractive power of simple, ablated PMMA lenses, e.g. by means of lensometers or the examination of two-dimensional patterns on fluence paper or foil. Thus, monitoring the system parameters is more accurate.

The invention may further be used to document the condition at least prior to or even during treatment, with very little effort, allowing a physician to easily prove a correct adjustment later.

In principle, the calibrating body may have any desired shape, as long as the surface of the calibrating body to be ablated and examined is sufficiently known prior to ablation and preferably corresponds to a predetermined shape. In one embodiment of the method according to the invention, it is preferred that, for ablation, a calibrating body is used which is plate-shaped in the region to be ablated. In the non-ablated condition, such calibrating bodies have no aberrations during examination and, therefore, allow a simple determination of the system parameters. Moreover, they can be manufactured very easily and inexpensively with a sufficiently accurately defined surface.

Alternatively, it is preferred—in particular, for use in treatments in the field of refractive laser surgery on the eye or on the cornea—to use a calibrating body which has a spherical shape at least in the area to be ablated and to be examined. The curvature in this area preferably corresponds to the average corneal curvature of the eye. In this manner, results are obtained which can be very easily translated to the treatment of an eye. In particular, it is also possible to obtain information on the treatment system in a direction parallel to the direction of the treatment laser beam.

In order to enable particularly precise treatment, it is preferred to use a calibrating body which comprises a surface portion to be ablated at least partially having the shape of the corneal segment of the eye to be treated. Such a body may be obtained, for example, by examining a patient's eye by means of aberrometry or profilometry, and by corresponding pre-ablation of the calibrating body prior to using it in order to determine system parameters. This form of the calibrating body allows a very accurate transfer of the ablation results from the calibrating body to the cornea with only little error. Further, the ablation program used can thus be checked, by examining the quality of the calibrating body ablated by means of the ablation program intended for treatment.

The material of the calibrating body is basically freely selectable, as far as it can be ablated in a reproducible manner. In particular, when using aberrometry, the material is preferably optically homogeneous, at least prior to ablation, in the range of the wavelength used for examination. In particular, gelatin may be used as a very inexpensive material, for example. However, for advantageous ablation behavior and simple manufacture, it is preferred to use a polymethylmethacrylate calibrating body as the calibrating body.

In order for the examination data to remain undistorted, the treatment laser beam should usually not enter the examining unit. It is therefore preferred to use a calibrating body which is not transmitting for a wavelength of optical radiation used for measurement in aberrometry or profilometry. The calibrating body then only allows little or no treatment radiation to enter the examining unit. Use is preferably made of polymethylmethacrylate (PMMA), which is characterized by being non-transparent at a wavelength in the region of 193 nm, i.e. the wavelength of excimer lasers used in typical treatment systems.

Alternatively, it is preferred to use a filter for separation of the treatment laser beam and of the optical radiation used for examination. Therefore, it is advantageous for the system parameter determining device according to the invention, to arrange a filter, which is non-transmitting for optical radiation having the polarization and/or the wavelength of the treatment laser beam, in the beam path of the examining unit preceding a photo detector of the examining unit. The filter may have a wavelength-specific and/or—when using a polarized treatment laser beam—polarization-specific effect and is transmitting, in particular, for the optical radiation used for examination.

The calibrating body or the holder for the calibrating body, respectively, can be arranged basically in any desired manner. However, it is preferred that, during examination, the calibrating body be arranged in the working plane of the treatment system or in a plane equivalent or conjugated thereto. An equivalent plane is understood to be a plane in which the treatment laser beam or the partial beam essentially has the same properties as in the working plane. For example, a beam deflector may be provided in the beam path of the treatment system, said deflector deflecting the treatment laser beam or only a partial beam toward the equivalent plane, with the beam traveling the same optical distance. This will result in ablation profiles which represent the conditions of treatment with particular accuracy, and in actual values of the system parameters obtained therefrom.

For this purpose, it is preferred, in one embodiment of the system parameter determining device according to the invention or of the system according to the invention, that the holder be movable in and out of a treatment beam path of the treatment system. Particularly preferably, the holder, when arranged in the treatment beam path, is arranged in the working plane of the treatment system. In particular, the holder, held on a carrier, may then be pivoted or shifted. In this manner, the calibrating body can be very easily and accurately placed in the treatment beam path and, in particular, in what will later be the working plane of the treatment system. The holder may be moved manually or, preferably, by a drive. Particularly preferably, the drive is controllable by the control unit of the treatment system such that the holder is automatically movable in and out of the treatment beam path.

Alternatively, when arranging the calibrating body in the treatment beam path, it is preferred, in the treatment system according to the invention, that the examining unit be supported, as a unit with the holder, at or on a carrier of the treatment system and be movable in and out of the treatment beam path. In particular, the examining unit comprising the aberrometer and/or profilometer and the holder may be pivoted or shifted. In this manner, the calibrating body can be very easily and accurately held in the examining unit or in the aberrometer and/or profilometer, respectively, which can increase the accuracy of examination. Even if used several times, this arrangement provides a very accurate alignment of the examining unit and the holder, and thus also of the calibrating body in the holder, relative to each other, so that errors of alignment or of adjustment are very easily avoided. In doing so, the examining unit comprising the holder may be moved manually or, preferably, by a drive. Particularly preferably, the drive is controllable by the control unit of the treatment system such that the examining unit comprising the holder is automatically movable in and out of the treatment beam path.

In principle, the method according to the invention may be effected, independent of a treatment, for calibration at the factory, for control during maintenance or for calibration prior to treatment, for example. However, it is particularly favorable to execute said method during treatment of the eye. In doing so, the system parameter may be determined in a continuous manner or by alternation with single partial treatment steps. In this case, the actual values of the system parameter or the deviations from the desired value of the system parameter, respectively, are present in corresponding time intervals as a function of the frequency of the examination, in particular the detection frequency of the aberrometer or of the profilometer. This allows to determine, in particular, fluctuations of the system parameter during treatment, e.g. drift in the deflecting unit, fluence fluctuations, etc.

For detection, the holder can be moved in and out of the treatment beam path. It is mechanically simpler to direct the treatment laser beam onto the eye and onto the calibrating body in an alternating manner. In the system according to the invention, it is preferred, for this purpose, that a deflecting device comprising, for example, a mirror, which is movable between two positions, be arranged such that the treatment laser beam is incident on the eye or on the calibrating body. In this manner, the calibrating body need not be moved. Further, the treatment laser beam can be used, unweakened, for treatment. Basically, operation of the deflecting unit, e.g. movement of the mirror, may be effected manually. An automatic drive is provided for use during treatment. Deflection is then preferably synchronized with the emission of the treatment laser beam. The same ablation program may then be carried out on the cornea and on the calibrating body in a substantially synchronous manner. The use of a mirror is particularly easy if the mirror is rotatably supported, because in this manner, deflection will be effected in a mechanically and constructionally simple manner.

In a different embodiment of the method according to the invention, it is preferred that the treatment laser beam be split and that one partial beam be used to ablate the calibrating body and the other partial beam be used to treat the eye. In the system according to the invention, it is convenient to arrange a beam splitter in the treatment beam path of the treatment system for this purpose, which splits off a partial beam from the treatment laser beam for ablation of the calibrating body and which is held in the holder arranged outside the treatment beam path. This allows to check the system parameters during treatment. When determining the system parameter, the optical properties of the beam splitter, as far as they affect the properties of the partial beam, should be considered. A semi-transparent mirror may be used as the beam splitter.

Particularly preferably, the aforementioned deflecting device and/or the beam splitter is arranged following focusing optics or the deflecting unit of the treatment system. In this manner, system parameters can also be determined for the focusing optics and the deflecting unit. Further, when using a beam splitter, the partial beam of the treatment laser beam used for ablation of the calibrating body can simply be controlled by the same ablation program as the treatment laser beam treating the eye.

Examination of the surface of the calibrating body may basically be effected using a separate examining unit, which is independent of the treatment system. In order to minimize the constructional dimensions, the aberrometer or the profilometer of the examining unit can be integrated into the treatment system; in particular, the aberrometer and/or the profilometer may be securely connected to the treatment system. Particularly preferably, the aberrometer and/or the profilometer for the examining unit can be used in the treatment system for examination of the eye, because this results in a particularly compact treatment system, which, at the same time, has an inexpensive design. This embodiment is particularly advantageous in combination with a calibrating body holder that is movable in and out of the treatment beam path.

In order to achieve a very compact design, it is particularly preferred that a measurement ray bundle, which is used to examine the calibrating body, be coupled, colinear to the treatment laser beam or to a partial beam split off therefrom, into the beam path of the treatment laser beam or of the partial beam for ablation of the calibrating body. In the treatment system according to the invention, a measurement beam path of the examining unit is then at least partially colinear to a beam path of the treatment laser beam.

According to the invention, basically any method of aberrometry or, in the examining unit, any aberrometer may be used. In order to even determine aberrations of higher orders in a simple and reliable manner, it is preferred, however, to acquire and evaluate data of a wavefront influenced by the ablated calibrating body, or a change in the wavefront, in order to examine the ablation condition of the ablated calibrating body. In the system parameter determining device according to the invention, it is thus preferred that the examining unit comprise an aberrometer working on the basis of wavefront data.

For this purpose, basically any suitable aberrometers can be used. For example, the aberrometer may operate interferometrically and comprise, for example, a Twyman-Green sensor. However, preferably, aberrometers using geometrically operating sensors, e.g. Tscherning aberrometers or systems operating on the skiascope principle, are used. The aberrometer may also comprise a Shack-Hartmann sensor. In addition to a simple design, such aberrometers have a very high resolution and a high detection frequency.

In principle, any desired profilometry methods or devices may be used. However, in the method according to the invention, it is preferred that an optically operating method be used for profilometry and that, in the system parameter determining device or in the treatment system, the examining unit comprise an optically operating profilometer. Such profilometry methods or profilometers, respectively, allow quick, contact-free determination of elevation profiles or of topographical data. As profilometers, in particular, Placido ring topography instruments for ophthalmology or other optical surface profilometers may be used.

For precise monitoring, it is advantageous, if information on a plurality of the system parameters is simultaneously acquired by one single measurement. Therefore, it is preferred, in the method according to the invention, to respectively determine, from the same examination data, an actual value and/or a deviation from a corresponding desired value for at least two system parameters. These may be selected, in particular, from the above-mentioned list of system parameters. Accordingly, it is preferred, in the system parameter determining device according to the invention, that the evaluating unit be adapted for respectively determining, from the same examination data for at least two system parameters, an actual value and/or the deviation from a corresponding desired value. Determination on the basis of the same examination data may be effected essentially simultaneously, so that no additional time expenditure is generated. Particularly preferably, the actual values or the deviations from corresponding desired values can be suitably determined for more than two system parameters in the preferred embodiments and in further embodiments described above and below with regard to one system parameter.

In order to detect system parameters which vary over time, all decisive system parameters of the treatment system are preferably determined repeatedly at successive times.

The actual value of the system parameter or actual values of the system parameters and/or, in particular, the deviation from the desired value or deviations of the system parameters from the desired values can be determined in different ways.

On the one hand, the actual value of the system parameter may be respectively determined in absolute terms from the examination data, to which end theoretical or empirically determined relations can be used. Said actual value is then compared to a predetermined desired value.

As an alternative, it is possible to determine the deviation of the actual value of the system parameter from the desired value or the deviations of the actual values of the system parameters from the desired values on the basis of a comparison of the examination data with corresponding reference data. For this purpose, it is convenient, in the system parameter determining device according to the invention, to adapt the evaluating unit for determining the deviation of the actual value of the system parameter from the desired value or the deviations of the actual values of the system parameters from the desired values by comparing the examination data with corresponding reference data. Such comparison is generally easier to carry out, because the absolute desired values need not necessarily be explicitly known. Also, an actual value may be determined in absolute terms for one system parameter, while a deviation from a desired value may be determined for another system parameter.

In a preferred embodiment of the invention, the reference data are given by corresponding theoretical values or by data which are previously determined in a predetermined treatment system, wherein the system parameters have the desired values, by ablation and measurement of a calibrating body. This solution is possible with fixed ablation patterns, e.g. with specific ablation data for well-defined higher aberration terms. In this connection, it is preferred, in the system parameter determining device according to the invention, that said device comprise a memory for storage of the reference data.

In an embodiment of the method according to the invention, a reference body is advantageously examined after application of a predetermined ablation pattern by aberrometry and/or profilometry, and the examination data thus obtained are used as reference data. The reference body was conveniently obtained by ablation of a body corresponding to the calibrating body, using a treatment system wherein the system parameters have the predetermined desired values. The reference body may have been obtained directly by ablation or by transferring the shape of a previously ablated body. In this manner, the reference data may simply be newly generated in each case. In particular, corresponding reference bodies may be used for different calibrating bodies. Further, inherent properties of the aberrometer and/or of the profilometer are thus easily taken into consideration.

In the system parameter determining device and treatment system according to the invention, a reference body comprising a predetermined reference ablation pattern may be profitably used. The reference body is movable into a measurement beam path of the examining unit. This reference body may be introduced, manually, or preferably automatically, into the examining unit and measured or examined, any time and with great ease. The examination data of the reference body, which have been obtained in this manner, then represent the reference data for comparison with the data of the body ablated before or during treatment.

In applications, where the actual values and/or deviations from the desired values of the system parameters are continuously determined during treatment, the use of a new calibrating body for each new determination in order to achieve greater accuracy can be dispensed with if the method is carried out in a cyclic manner and reference data for the current cycle are determined from examination data of a preceding cycle. In the system parameter determining device according to the invention, it is preferred, for this purpose, that the evaluating unit be adapted to determine reference data for the current cycle from examination data of a preceding cycle in the case of cyclic acquisition of examination data. For such determination, in addition to the ablation program, use can be made, if the system parameters are suitably corrected, of the desired values of the system parameters or, otherwise, of the actual values between two cycles.

Different approaches may be used in order to compare the examination data of the currently generated and measured calibrating body with the reference data or the examination data of the measured reference body. According to the type of data sets, e.g. modally or zonally reconstructed wavefront representations or topographical elevation data, suitable methods include, for example, difference methods, differential methods, moment methods, or other generally known mathematical methods and their combinations, in order to compare the data measured and determined during examination with the reference data and to determine, from any deviations between them, deviations of the system parameters for the treatment system and, as the case may be, to determine them quantitatively. The determined deviation of the system parameters from desired values can then be output.

The method or the device, respectively, may be further adapted for calibration of a system for treatment of an eye. For this purpose, it is preferred that, as a function of the determined actual value of the system parameter or of the determined actual values of the system parameters and/or of the deviation of the system parameter from the desired value or of the deviations of the system parameters from the desired values, at least one correction parameter be determined for the treatment system, said correction parameter being suitable to reduce deviations from a desired condition or desired function. For this purpose, the system parameter determining device comprises a correction value determining unit which, as a function of the determined actual value of the system parameter or of the determined actual values of the system parameters and/or of the deviation of the system parameter from the desired value or of the deviations of the system parameters from the desired values, determines at least one correction parameter for the treatment system, said correction parameter being suitable to reduce deviations from a desired condition or desired function. In the treatment system, it is preferred that the system parameter determining device or the control unit comprise a correction value determining unit which, as a function of the determined actual value of the system parameter or of the determined actual values of the system parameters and/or of the deviation of the system parameter from the desired value or of the deviations of the system parameters from the desired values, determines at least one correction parameter for the treatment system, said correction parameter being suitable to reduce deviations from a desired condition or desired function. The correction parameters may be, in particular, manipulated variables for adjusting units of the treatment system, by which adjusting units the corresponding system parameters can be changed. For example, the desired condition may be given by corresponding desired values of the system parameters, while the desired function may be given by forming a predetermined ablation pattern. For example, a defined calibration condition of the treatment system can be set in the factory. However, it is also possible, during or after use of the treatment system, to restore the calibration condition set in the factory.

It is then further preferred, in the method according to the invention, to change at least one setting of an adjusting unit of the treatment system, as a function of the determined actual value of the system parameter or of the determined values of the system parameters or of its deviation from the desired value or the deviations of the system parameters from the desired values, in order to reduce deviations from a desired condition or desired function. The adjusting unit may be, in particular, an electrical and/or optical and/or mechanical and/or electromechanical and/or optomechanical adjusting unit of the treatment system. This allows calibration to be effected with ease. On the whole, this also enables closed-loop control.

A deviation of the system parameter from a desired value can basically be removed manually by an operator, by a corresponding correction of the treatment system.

For automatic closed-loop control, it is preferred to change the setting of the treatment system automatically, on the basis of the actual value of the system parameter or of the actual values of the system parameters or of the deviation of the system parameter from the desired value or of the deviations of the system parameters from the desired values, in order to reduce the deviation between actual value and desired value or the deviations between actual values and desired values. For this purpose, the evaluating unit may be connected to the control unit, and the evaluating unit and/or control unit may be provided such that, on the basis of the actual value of the system parameter or the deviation of the system parameter from the desired value, the setting of the treatment system can be changed automatically so as to reduce the deviation between actual value and desired value. Thus, re-adjustment of the system parameter is achieved by adjusting units or by adjustments of the treatment system. In particular, examination and re-adjustment during treatment allows to thus achieve high stability of the system parameters against fluctuations and/or drift, thus allowing an enhancement of the precision of the actual treatment.

Re-adjustment serves the purpose of achieving a predetermined ablation on the cornea of the eye. Therefore, it is alternatively or additionally preferred, in the method according to the invention, to change a program or at least one parameter value for the program for changing the position and/or intensity of the treatment laser beam over time, according to the actual value and/or the deviation of the system parameter from the desired value, in order to achieve a predetermined ablation profile. Thus, the treatment system is not necessarily adapted, for example, to the function of the treatment laser and/or of the deflecting unit, but the ablation program is suitably adjusted such that the currently present system parameters allow the desired ablation profile to be obtained on the cornea. For this purpose, it is preferred, in the treatment system according to the invention, that the evaluating unit be connected to the control unit and that the control unit be adapted such that, on the basis of the actual value and/or the deviation of the system parameter from the desired value, a program or at least one parameter value for the program for changing the position and/or intensity of the treatment laser beam over time is variable in order to achieve a predetermined ablation profile. For this purpose, in particular, the evaluating unit may output suitable correction values to the control unit. In particular, such change may be effected by changing the values of parameters of a control program as a function of the actual value of the system parameter or of the deviation of the system parameter from the desired value and the desired ablation profile. The basis for this may be theoretically or empirically determined relationships between the ablation profile and the system parameters. For example, a dependence, known per se, of the ablation depth from the treatment laser fluence or the shape and depth of the transition zone or the deviations in shape of certain higher aberrations generated in the calibrating body or in the eye as a function of the spot shape may be utilized for this purpose.

The two last-mentioned embodiments of the invention comprising a re-adjustment of system parameters and a change in the ablation program may also be combined. This has the advantage that the system parameters to be adjusted can be limited to the most relevant system parameters and/or those system parameters whose adjustment is technically possible with little expenditure and that deviations of the actual values of other system parameters from corresponding desired values are accounted for by adjustment of the ablation program.

This calibration method, which can be integrated into the treatment system, increases the precision of the treatment system and frees the operator from tedious manual calibration operations while excluding subjective errors of evaluation, such as those which may occur when inspecting fluence papers or fluence foils, for example.

Preferably, the actual ablation of the calibrating body may be used directly to draw conclusions as to the ablation condition achieved on the patient's cornea, said actual ablation having been determined during treatment. Thus, ablation can be dynamically controlled until the optimal target ablation is achieved on the calibrating body, which ablation will also lead to optimal treatment of the patient with largely known relationships between the ablation of the body and of the cornea. As a desired ablation for the calibrating body according to this procedure, the desired ablation determined prior to treatment is suitable, which is converted with regard to the ratios of the body.

The aspects of the present invention explained above related to the characterization, calibration/adjustment and control of laser systems in refractive laser surgery made possible by aberrometry. However, the present invention can also be used in any other therapeutic method of (laser) surgery, wherein biological material is to be removed and wherein equivalent methods of material removal are used.

Moreover, as explained above, the method is not limited to measurement and use of aberration data, but may also be modified such that topography data (or profilometry data) are used. For this purpose, the examining unit 8 may use a profilometer instead of an aberrometer.

BRIEF DESCRIPTION OF THE DRAWINGS

The invention will be explained in more detail below, by way of example and with reference to the drawings, wherein:

FIG. 1 shows a schematic representation of a treatment system and of a system parameter determining device according to a first preferred embodiment of the invention;

FIG. 2 shows a schematic representation of an aberrometer of the system parameter determining device of FIG. 1;

FIG. 5 shows measured aberrations in the form of profile elevation values in a greyscale representation in the case of decentration of a deflecting unit of the treatment system of FIG. 1 relative to an eye movement tracking system of the treatment system of FIG. 1, as well as corresponding values of Zernike coefficients;

FIG. 6 shows results of simulations for aberrations on ablated calibrating bodies, with a rotation of the axes of a deflecting unit of the treatment system according to FIG. 1 relative to their desired positions, including representations of profile elevations as greyscale values, corresponding Zernike coefficients and the respective angles of rotation;

FIG. 7 shows results of measurements of the influence of changes in fluence on aberration, including representations of profile elevations as greyscale values and corresponding Zernike coefficients;

DETAILED DESCRIPTION

Figure 3:
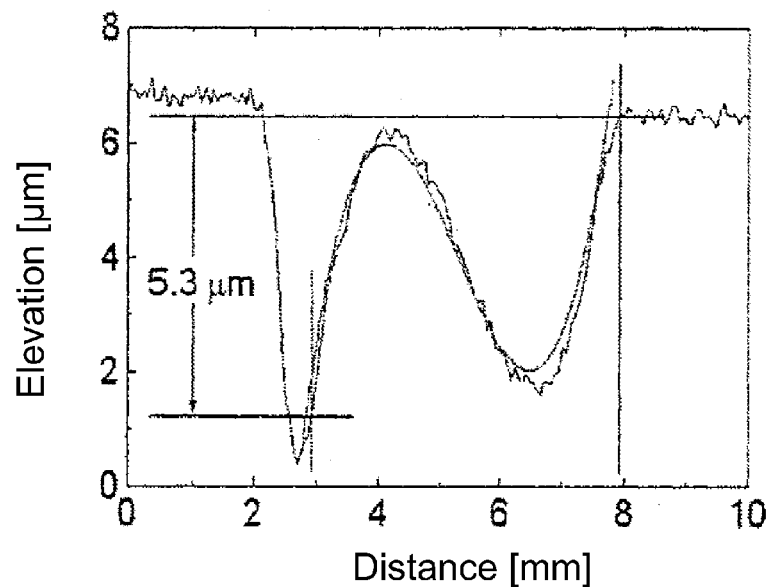
FIG. 3 shows graphic representations of a typical, theoretically determined cross-section and of a measured cross-section for a Zernike-Coma term generated by means of excimer laser ablation of a PMMA calibrating body.

In FIG. 1, a treatment system 1 for refractive laser surgery on the eye comprises: an excimer laser 2, which controllably emits a treatment laser beam 3; adjustable focusing optics 4 for focusing the treatment, laser beam emitted by the excimer laser 2; a deflecting unit 5, by means of which the treatment laser beam 3 is deflectable according to predetermined deflection signals; a system for tracking an eye movement, which is not shown in the Figures, and a control unit 6, which is connected to the excimer laser 2, the focusing optics 4, the system for tracking the eye movement and the deflecting unit 5, via corresponding signal links, and which is adapted to emit corresponding control signals to adjusting units, not shown in the Figures, as a function of a predetermined ablation program and movement data of the eye movement tracking system. Treatment systems of this kind are principally known, so that the treatment system shall not be described in detail below. An example of such a treatment system is the MEL 70 excimer laser system from Carl Zeiss Meditec AG, Jena, Germany.

Further, a system parameter determining device 7 for determining actual values of system parameters of the treatment system 1 or deviations of these parameters from desired values, also referred to, for simplification, as a system parameter determining device, is provided, which comprises an examining unit 8 and an evaluating unit 9.

A holder 10 for a calibrating body 11 mounted in a mount, not shown in the Figures, is arranged at a position in the treatment beam path of the treatment system 1. The holder 10 can be regarded as being associated with the treatment system 1.

The excimer laser 2 may be provided as an ArF excimer laser having a wavelength of 193 nm, which emits the treatment laser beam 3, e.g. in the form of pulses of predetermined duration and intensity, as a function of corresponding control signals from the control unit 6.

For focusing or imaging, respectively, of the treatment laser beam 3 onto a working plane, the focusing optics 4 are adjustable in focal length and/or position. Although they are schematically represented in the Figures by only one lens, they do, in fact, comprise further lenses and, as the case may be, also ray bundle-limiting means, such as stops, for example. For adjustment of the focusing optics 4, actuating drives (not shown) controllable via corresponding signals are provided.

The deflecting unit 5 comprises two beam-redirecting or beam-deflecting elements, e.g. mirrors, by means of which the focused treatment laser beam 3 is deflectable in two spatial directions, said elements being directable by two corresponding actuating drives.

The system parameter determining device 7 or the examining unit 8, respectively, comprises an aberrometer 12, which is schematically shown in more detail, in FIG. 2, and which also includes a measurement data processing unit 13 in addition to the optical devices. The aberrometer 12 is provided for determining aberration by examining wavefronts by means of a Shack-Hartmann sensor 20. A measurement light source 14, which is a super-luminescence diode in the example, generates a measurement ray bundle 15, which is transformed by illumination optics 16 into an essentially parallel measurement ray bundle 15 having an essentially planar wavefront, and, in the example, is directed, via a not absolutely required beam deflection 17, onto an ablated calibrating body 11 to be examined and held in a holder 18 of the aberrometer.

The holder 18 is designed like the holder 10 for reception of a mounted calibrating body 11.

The measurement ray bundle 15 with its essentially planar wavefront passes through the calibrating body 11 in the holder 10, is deformed thereby, and is then imaged onto the Hartmann-Shack sensor via sensor optics 19. When the parallel measurement ray bundle 15 passes through the treated, transparent calibrating body 11, aberrations are generated, which are linked in a physically definite manner with the optical path difference, which locally varies in a plane of the calibrating body 11 orthogonal to the mean direction of the measurement ray bundle 15, i.e. with the surface topography of the calibrating body 11.

In the embodiment, the Hartmann-Shack sensor 20 is formed by a microlens field 21 and a CCD camera 22, which detects the measurement ray bundle 15 being imaged onto the photodetector surface of the CCD camera 22 by the microlens field 21 and converts it into a corresponding intensity image in the form of a field of intensity values.

The sensor optics 19 are provided and arranged such that the photodector field of the CCD camera 22 is conjugate to an ablated surface of the calibrating body 11. In the example, the sensor optics 19 are realized as an imaging telescope.

The intensity image detected by the CCD camera 22 is then transmitted to the measurement data processing unit 13 via a suitable data link, said measurement data processing unit analyzing the intensity images in a computer-assisted manner according to well-known methods and determining the aberrations as examination data. For this purpose, the measurement data processing unit 13 comprises a corresponding input interface, a microprocessor including a memory in which, inter alia, a corresponding measurement data processing program is stored, and an output interface 23 via which the examination data are output.

The evaluating unit 9 is connected to the output interface 23 of the aberrometer 12 or the measurement data processing unit 13, respectively, in order to determine, from the examination data, actual values of system parameters and/or deviations of the system parameter values from desired values and to output them via an interface 24. In particular, in the present embodiment, the evaluating unit 9 comprises a memory, not shown in FIG. 1, in which memory reference data for comparison with determined examination data are stored.

The evaluating unit 9 may generally be integrated in the measurement data processing unit 13 in the sense that the corresponding functions are provided by software modules running on the same microprocessor, which is connected to a memory and suitable interfaces. However, in the example, there are provided physically separate units, so that the evaluating unit 9 also comprises input and output interfaces, a memory and a microprocessor cooperating with said interfaces and said memory, said microprocessor being programmed to carry out the corresponding step of the method.

In order to carry out the method of the invention according to a first preferred embodiment of the invention, a transparent PMMA calibrating body 11 in the holder 10 is ablated by the treatment laser beam 3, according to a predetermined ablation program stored in the control unit 6, by guiding the treatment laser beam 3 over corresponding surface areas of the calibrating body 11, the treatment laser beam 3 being pulsed according to a time program. Alternatively, use may also be made of a calibrating body 11, whose refractive index may be locally varied by laser radiation, e.g. a calibrating body of UV-modifiable material. In a simple realization, the calibrating body is a plane-parallel plate; however, it may also be spherically pre-formed.

The ablation program is selected such that the ablated calibrating body 11 causes suitable higher aberrations which are characterized by high spatial frequencies and optionally missing rotation symmetry.

The ablated calibrating body 11 is then manually removed from the holder 10 and inserted into the holder 18 in the aberrometer 12. After that, wavefront analysis of the ablated surface of the calibrating body 11 is carried out. In doing so, suitable aberrations are determined, in the measurement data processing unit 13, as examination data from the intensity images of the Shack-Hartmann sensor 20.

The examination data are then transmitted to the evaluating unit 9, where actual values of system parameters and/or deviations of the system parameters from desired values are determined from the examination data and output via the interface 24. As a parameter combination, parameters of the eye movement tracking unit or the spot size, in particular the spot diameter, may be used. Ablation of the test body may also be effected on-line with a coupled-out portion of the beam used for treatment.

The system parameters are determined by comparing the measured examination data, i.e. the actual aberrations, of the ablated calibrating body 11 with reference data for the desired aberrations in the case of proper calibration, which reference data have been determined in connection with the ablation program and the shape of the non-ablated calibrating body 11 and are stored in the evaluating unit 9 in order to effect said comparison.

There are definite relations between the various possible deviations between desired and actual data or aberrations, respectively, and the system parameters, such as fluence, spot shape, offset of the deflecting unit 5, etc., for example. These connections may be determined theoretically, but also empirically.

The results thus obtained for the actual values of the system parameters now allow conclusions as to the calibration condition of the treatment system 1 to be drawn directly. If the actual values of the system parameters determined from the aberrations of the calibrating body 11 deviate not at all or only slightly, i.e. by an absolute difference of less than a respectively predetermined threshold value, from the desired values of the calibration effected in the factory, the system is in a safe operating condition and ablations can be effected in an accurately directed manner.

Otherwise, it may be derived from the determined deviations of the actual values of the system parameters from the desired values of the system parameters that the treatment system 1 is not correctly calibrated.

It is now possible to derive values for correction parameters as well, in knowledge of the individual actual values of the system parameters, said correction parameters being variables in predetermined adjustment or setting rules, e.g. for re-adjustment of the deflecting unit 5 or of the focusing optics 4, by which the deviations from the actually desired calibration condition are eliminated. The connections between values of the correction parameters and the deviation of the system parameters from their desired values may be determined, according to the type of system parameter deductively, by considerations of theoretical physics, or empirically. The deviations of an actual value of a given system parameter from the desired value are thus eliminated by changing a correlated, defined set of correction parameters for adjusting units or for settings of closed-loop control parameters, etc.

Setting the actual values of certain system parameters back to the desired values is done, in this embodiment, by manual adjustments of the various components by technical staff. This method is suitable, for example, for factory-side calibration of the system at the factory. Moreover, these methods may also be employed for re-calibration by service technicians.

The treatment system 1 to be tested may be, for example, the MEL 80 excimer laser system from Carl Zeiss Meditec AG, Jena, Germany. This system is then used to generate a specific ablation profile on mounted PMMA calibrating bodies, which are positioned in the ablation beam of the treatment system in a defined manner. The ablated calibrating body is then inserted into a test eye unit, which is mountable in a defined manner to an aberrometer, e.g. a WASCA Wavefront Analyzer from Carl Zeiss Meditec AG, Jena, Germany.

The test eye unit comprises the holder 18 for the calibrating body 1, which is arranged such that the calibrating body, after mounting of the test eye unit, is held in a position relative to the aberrometer 12 in which, otherwise, an eye to be examined would be positioned. By the measurement of the ablated, transparent calibrating body, the aberrations caused by ablation are increased.

FIG. 3 shows graphic representations of a typical, theoretically determined cross-section and of a measured cross-section through the center of the test body for a Zernike-Coma term $Z(3, 1)$ generated by means of excimer laser ablation in a PMMA calibrating body. The noisy curve indicates the measurement of the surface by means of optical profilometry, and the smooth curve shows the section through the representation of the theoretically predetermined Zernike polynomial $Z(3,1)$ (notation according to Malacara, "Optical Shop Testing", $2^{nd}$ edition, in Wiley, 1992).

In the following, it will be demonstrated, by three examples, on what basis system parameters can be derived from aberrations. All aberrations mentioned are represented by Zernike coefficients in a mode expansion using Zernike polynomials, which coefficients are considered to be functions of the system parameters. The values indicated for the Zernike coefficients correspond to the differences in beam path length according to the Malacara notation.

As a first example, decentration between an eye movement tracking system ("eye tracking" system) and a zero position of the deflecting unit 5 for deflection of the treatment laser beam is chosen.

Figure 4:
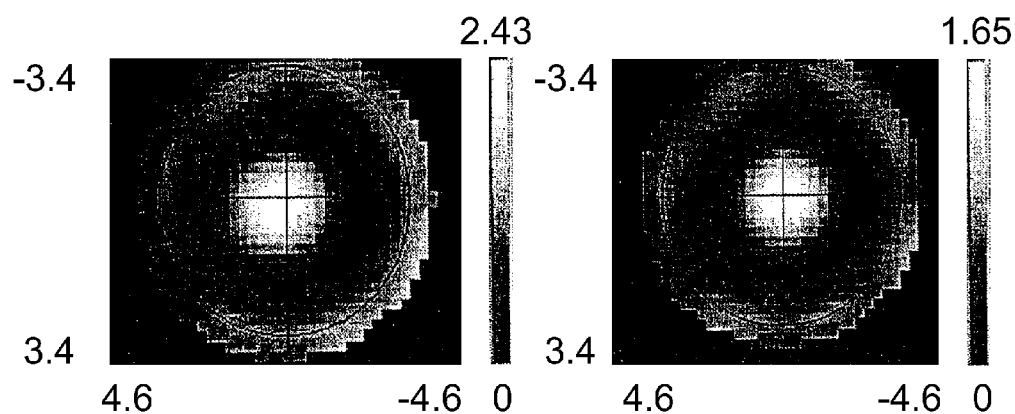
FIG. 4 shows measured aberrations in the form of profile elevation values in a greyscale representation in the case of decentration of a deflecting unit of the treatment system of FIG. 1 relative to an eye movement tracking system of the treatment system of FIG. 1.

FIG. 4 shows the data of the PMMA calibrating bodies for two different centrations, which data have been measured with the above-mentioned aberrometer. In the image on the left, the zero position of the deflecting unit of the treatment system during ablation was not in agreement with the eye tracking system, which is shown directly by a comparison with the correctly adjusted system (image on the right).

The basis of the comparison is illustrated in the image sequence of FIG. 5 by the third and fourth order aberrations for calibrating bodies which have been ablated with different decentrations.

For the desired ablations to be generated on the calibrating body by the above-mentioned treatment system, the first-order spherical aberration, i.e. one having Zernike coefficient $Z(40)$, was selected.

From top to bottom, FIG. 5 shows different decentrations. For a fixed analytical diameter, Zernike amplitudes of an expansion of the aberrations of the ablated calibrating bodies in Zernike polynomials have been determined.

FIG. 5, center, shows greyscale elevation representations of the surface topography determined by means of wavefront analysis. Next to them, on the right, the aberrations or Zernicke coefficients, determined by wavefront analysis or from the surface topography, respectively, are indicated as values for the optical path difference according to the Malacara notation in units of nanometers.

The ablated calibrating body for the centered position, i.e. the uppermost greyscale elevation representation of the measured wavefront in FIG. 5 (image 1), substantially shows a pure $Z(40)$ aberration term.

The other images 2-5 in FIG. 5 show decentrations, which always lead to a well-defined superposition of the spherical aberration $Z(40)$ with substantially one dominating coma term, i.e., in the example, Z(3, −1) or Z(3, 1), respectively. It should be noted that, in the cases shown, decentrations in the range clearly below 500 μm were selected. Even such small decentrations result in clearly distinguishable decompositions using Zernike coefficients. Thus, the method is very sensitive. This allows all four cases of decentration to be clearly distinguished. In particular, the examination of the calibrating bodies and the representation of the results of examination in the form of Zernike coefficients of an expansion in Zernike polynomials allow to unambiguously infer decentration from the aberration proportions.

The knowledge and/or removal of such disadjustments is of particular importance in patient-specific corrections or "customized ablation". This is because corrections of higher-order visual defects and of local deficiencies in the cornea not only require the ablation to be effected in a precisely centered manner, but also with the correct axis, i.e. in the correct direction, orthogonal to the optical axis of the cornea. For this purpose, use is made, for example, of so-called "limbus trackers", which recognize blood vessels and other structures on the iris and control the deflecting unit accordingly.

FIG. 6 shows an example of the sensitivity of higher aberrations to rotation. It shows the results of simulations for the aberrations on ablated calibrating bodies during rotation of the axes relative to their desired positions. In the upper line, greyscale elevation representations of the surface topography determined by means of wavefront analysis are shown; below it, aberrations or Zernike coefficients, respectively, determined by wavefront analysis or surface topography, respectively, are shown as values of the optical path length difference according to the Malacara notation, and the last line shows the respective angles of rotation during measurement or ablation.

Slight disadjustments, e.g. a drift, in the synchronization between the eye tracking system (limbus tracker), for example, and the deflecting unit lead to rotations of the ablation patterns in the ablated calibrating bodies, which can be instantly recognized by the development of the decomposition of the Zernike coefficients. The coefficients Z(4,4) and Z(4,−4) depend greatly on the angle of rotation, with at least one coefficient each having an absolute value far exceeding the absolute values of the other coefficients. This sensitivity can still be significantly increased over the example shown, by increasing the aberrations used.

Of course, in both examples, respectively different Zernike coefficients can be selected, which depend, in a relatively sensitive manner, on a special system parameter, but practically not on another system parameter. Thus, in the first example (FIG. 5), the coefficients Z (3, −1), Z (3,1) and Z (4,0) depend on the value of decentration, whereas, in the second example (FIG. 6), Zernike coefficients Z (4,4) and Z (4, −4), but not Z (4,0), depend on the value of the rotation of the axis. In this manner, these system parameters can be determined simultaneously, i.e. based, in particular, on the same set of examination data, independently of each other, with great accuracy.

A further example shows the sensitivity of the method according to the invention for determining the variation of fluence (cf. FIG. 7). Herein, an ablation program was used, which does not lead to a completely regular desired ablation pattern in the case of correct values of the system parameters, i.e. not a completely regular pattern, for example one which leads to a pure aberration term centered on the mathematical center of the correction data, but a different pattern with regard to the initial treatment axis is ablated on a PMMA body.

FIG. 7 shows results for ablation with two different fluence values. The upper diagram and the upper table show results for an ablation with a fluence that was approximately 1.8 times higher than the fluence which led to the results in the lower diagram and lower table.

As can be recognized from the comparison, a variation in fluence leads not only to a general variation in wavefront amplitude or to a similar absolute or relative change in the corresponding Zernike coefficients or in the ablation depth, while the contributions of certain aberrations remain unchanged. Rather, the composition of the aberrations or of the Zernike coefficients also varies in the sense that some Zernike coefficients assume values which are to be interpreted as zero, within the accuracy to be expected, so that some Zernike coefficients or corresponding Zernike polynomials do not contribute to the sum of the aberrations. In this case, the change in composition turns out to be well-defined and reproducible.

For instance, in the example shown in FIG. 7, the Zernike coefficient of the Z(6,2) component at high fluence as compared to the Zernike coefficient at low fluence varies by a factor of ca. 3, the Z(6,0) coefficient varies by a factor of about 10, the Z(4,4) coefficient varies by a factor of about 6 and, finally, the Z(4,2) coefficient varies by a factor of about 2.

Similar relations between the deviations, which occur between ablation patterns on calibrating bodies ablated with different values of a system parameter, and the corresponding actual values of the system parameter are found also in the variation of other system parameters, e.g. the working distance and the spot shape, which is caused, for example, by the typical asymmetry of the beam profiles in excimer lasers, etc.

The relations between the wavefront aberrations measured for the ablated calibrating body and the system parameters may depend to a certain degree on the, especially construction-related, particularities of the respectively used treatment system. In individual cases, they may have to be examined and determined for the particular system under consideration.

Corrective measures are now initiated using the determined deviations of the system parameters. In a first embodiment, the centration and axial position between the eye tracking system ("eye tracker" or "limbus tracker") and the deflecting unit could be corrected, for example, by suitable adjusting units or elements or by electronic control at the factory or manually, on site, by the service technician.

In other embodiments of the invention, the values of the system parameters may also be obtained otherwise than by analysis of Zernike coefficients. Thus, differential analysis of the wavefronts for different system parameters may also be used. In this respect, defined rules may also be established, which relate certain wavefronts or ablation patterns to certain system parameters.

In an alternative embodiment of the method and, thus, also of the evaluating unit 9, the determination of the actual values of these system parameters is effected directly by comparing the desired values and the actual values for the ablation profile achieved by ablation of the ablated calibrating body 11 in the form of topographical data, e.g. "elevation maps", "height maps", and the like, which are obtained by modal reconstruction from the aberrations determined by means of the aberrometer 12, or also by zonal reconstruction of the wavefront by means of numerical integration by methods known to the person skilled in the art. Conversion of elevation data of the ablated calibrating body surface to wavefront data, i.e. optical path differences, and vice versa, requires taking into account, among others, the difference in refractive index between the two media, air and PMMA. The optical path length OPL is defined as: $OPL = n \cdot L$, yielding, for the optical path length difference DOPL between PMMA and air, DOPL=$(n_{PMMA}-n_{air}) \cdot L$. Herein, L is the local thickness of the calibrating body, which leads directly onto the shape of the ablated surface of the PMMA calibrating body 11.

Figure 8:
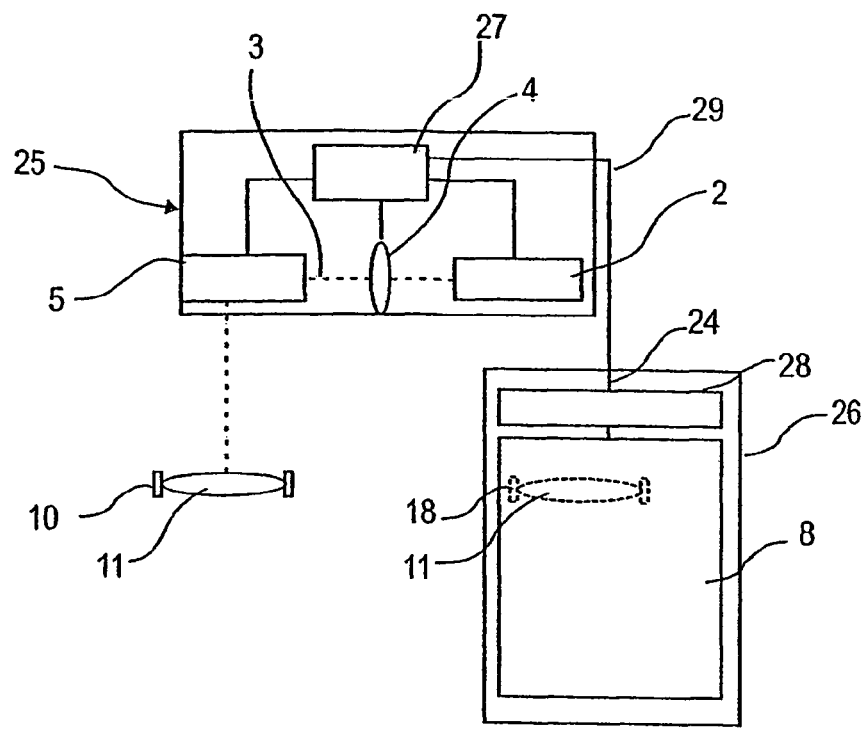
FIG. 8 shows a schematic representation of a treatment system and of a system parameter determining device according to a second preferred embodiment of the invention.

In a second preferred embodiment of the invention, the entire system formed by treatment system 25 and system parameter determining device 26, shown very schematically in FIG. 8, differs from the entire system of the first embodiment, formed by the treatment system 1 with holder 10 and the system parameter determining device 7, by a modified control unit 27 of the treatment system 25, a modified evaluating unit 28 of the system parameter determining device 26 and a data link 29 between the evaluating unit 28 and the control unit 27. Since the other components are unchanged, the same reference numerals are, therefore, used for the unmodified components, and the explanations for the embodiment apply.

The evaluating unit 28 is modified with regard to the evaluating unit 9 such that it automatically determines values for correction parameters or corresponding manipulated variables of the treatment system 25 from the examination data of the aberrometer 12 and outputs them to the treatment system via the data link 29, for which purpose it comprises a correction value determining unit not shown in the Figures. For this purpose, the evaluating unit 28 may comprise, in particular, a corresponding program module, said program module determining the corresponding calculations as a function of the structure, properties and manipulated variables of the treatment system.

The control unit 27 of the treatment system 25 comprises an interface for reception of values for the correction parameters or the manipulated variables and is further adapted to modify the manipulated variables according to the correction values received, for which purpose a corresponding program module may be provided here as well.

Whereas in the present embodiment the data link 29 is provided, in another embodiment the evaluating unit may also be adapted for outputting corresponding control signals and the control unit may be provided for processing the control signals.

Similar to the first embodiment, the measurement data processing unit 13 of the aberrometer 12 only provides the examination data, exemplified here by wavefront data or aberrations determined therefrom, e.g. in the form of Zernike coefficients and/or elevation data, which are output to the evaluating unit 28. There, first of all, the actual values of the system parameters are determined from which the desired value/actual value deviations are determined. Correction values for suitable correction parameters or manipulated variables of the treatment system 25 are then derived from the desired value/actual value deviations of the system parameters, for which purpose a corresponding procedure and corresponding data are used via the treatment system 25. These correction values are transmitted to the control unit 27 in the treatment system 25 via the data link 29. The control unit 27 provides the required actuating signals for open-loop or closed-loop control of adjusting units of the optical or electronic components of the treatment system, by which variables the system parameters are modified. Predetermining the desired values and the procedure for determining the correction values of the correction parameters in a suitable manner allows, for example, the factory-side calibration condition or system condition to be re-adjusted automatically.

In the present embodiment, it is possible, in particular, to use manipulated variables for adjusting units of the focusing optics 4, in the example, for displacing an imaging lens system, so as to modify the system parameters of working distance and correction of astigmatism of the laser beam, i.e. its beam shape. It is further possible to modify manipulated variables relating to mechanical/electrical adjusting units for modification of the deflecting unit 5, to adjusting units for the excimer laser head for regulation of fluence and to adjusting units for electromechanical regulation of laser beam attenuators of the treatment system 25, which are not shown in the Figures.

The determination of correction values or of values for the correction parameters, respectively, or manipulated variables, which an operator is required to effect in the method described in the first embodiment, and the corresponding adjustment of the treatment system 1 can now be effected automatically so that, as a result, a method for determining the actual values of the system parameters and for automatically calibrating the treatment system 25 is provided.

In the described second embodiment of the invention, the evaluating unit may be embodied, in particular, as a separate module. This has the advantage that different aberrometers and treatment systems can be used and for the respective aberrometer and/or the respective treatment system, variants which are device-typical can be taken into account by a corresponding hardware and/or software adjustment of the module.

In other embodiments, however, the evaluating unit 28 may also be integrated into the control unit 27 or, alternatively, into the measurement data processing unit 13. A separate unit is then omitted; rather, it may even suffice to provide corresponding program modules.

Figure 9:
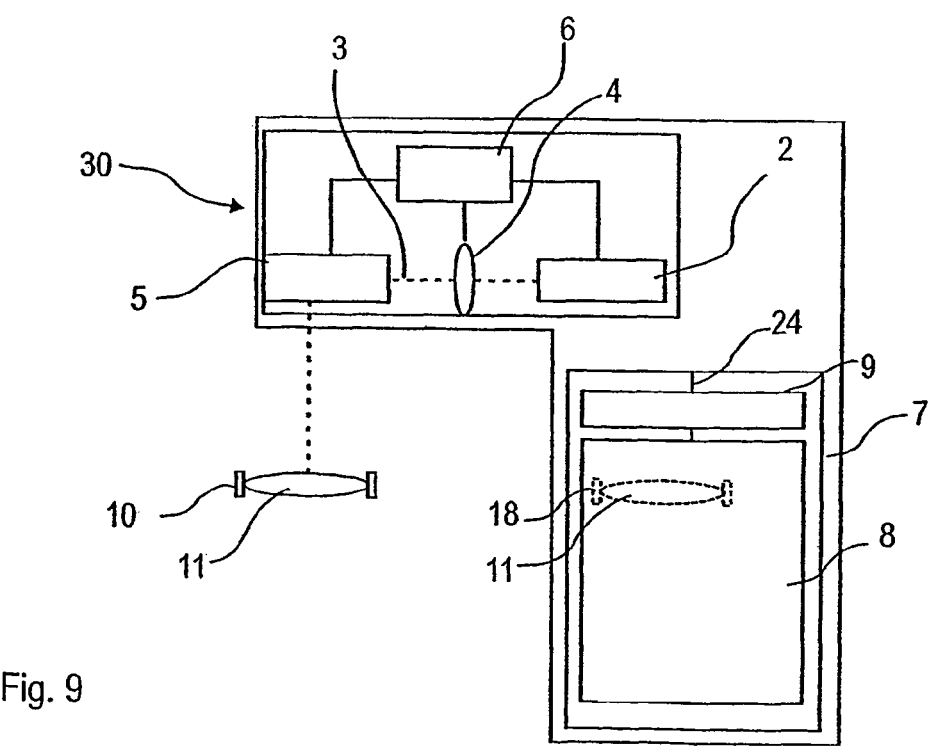
FIG. 9 shows a schematic representation of a treatment system with an integrated system parameter determining device according to a third preferred embodiment of the invention.

In a third embodiment illustrated in FIG. 9, the entire system comprising the treatment system and the system parameter determining device differs from the entire system consisting of the treatment device 1 with holder 10 and the system parameter determining device 7 of the first embodiment in that the system parameter determining device 7 is integrated into the treatment system 30 in a common housing.

This embodiment is interesting because most treatment systems for refractive corneal surgery nowadays are provided with aberrometers and/or profilometers or topography systems, respectively, for effecting patient-specific corrections ("customized ablation"). An aberrometer or profilometer may be used to measure aberrations of calibrating bodies, for example, after providing corresponding means, e.g. providing a holder corresponding to the holder 18 in the form of a test eye unit and optionally providing a program module for the measurement data processing unit 13. An on-site service technician can now use this means in order to examine calibrating bodies generated on-site with the treatment system.

For example, aberrometers having a structure like the aberrometer of FIG. 2 are suitable for integration into the treatment system. However, other aberrometers with other operating modes, such as Tscherning aberrometers or aberrometers based on skiascopy, are also suitable. Moreover, complete commercially available products, e.g. the above-mentioned WASCA Wavefront Analyzer or specially adapted OEM products, may be employed as well.

In a fourth embodiment, the treatment system 1 with the holder 10 and the integrated system parameter determining device 7 are, therefore, modified such that the evaluating unit 9 is replaced with the evaluating unit 28 comprising the correction value determining unit. However, the evaluating unit is realized by a suitable program module for the measurement data processing unit 13 in the form of additional software. By means of the program module which runs in the measurement data processing unit, system parameters and correction parameters are determined. These parameters allow the on-site technician to effect quick and comprehensive changes, in particular changes which are well-defined by the correction parameters, to the treatment system. This increases the safety and accuracy with which treatment systems can be checked and optimally adjusted.

In a fifth embodiment of the invention, the entire system consisting of the treatment system and of the system parameter determining device according to the third or fourth embodiment is modified in terms of handling the calibrating body.

While, in that case, the calibrating body 11 was manually placed in the holder 10 for ablation and in the holder 18 for measurement, the aberrometer 12 including the holder 18 is now held on the treatment system so as to be movable relative to the treatment system 46, which otherwise corresponds to the treatment system 1, such that a calibrating body held in the holder 18 is movable, for ablation, into the treatment beam path of the treatment system 46, i.e. into the treatment laser beam 3.

Figure 10:
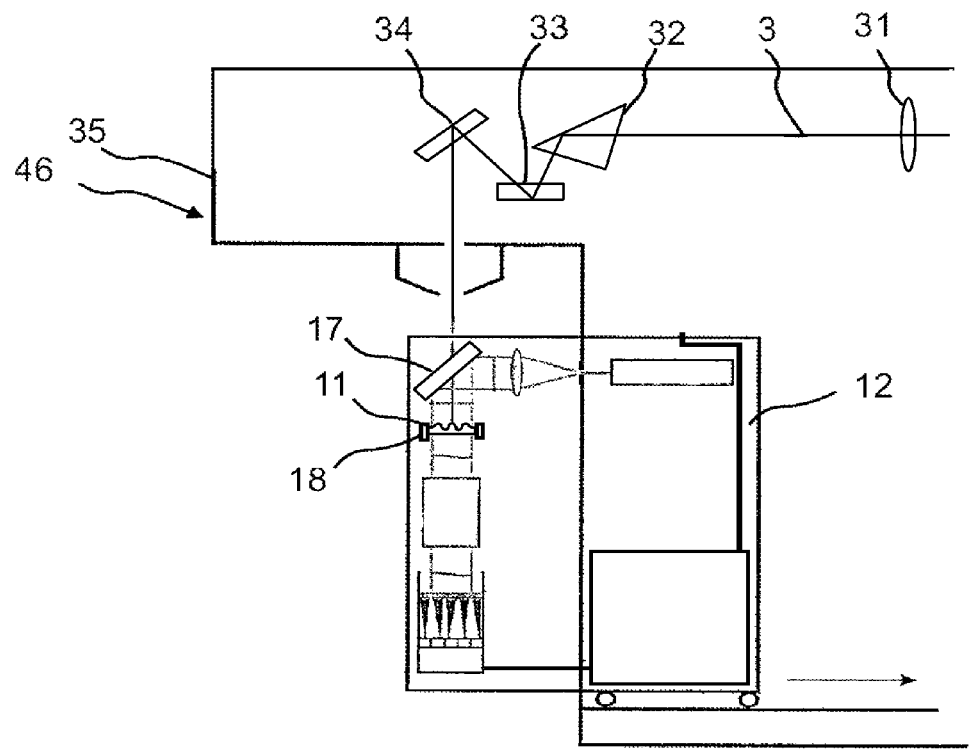
FIG. 10 shows a schematic partial representation of a treatment system comprising a system parameter determining device, which includes a movable aberrometer, according to a fifth preferred embodiment of the invention.

In the example shown in FIG. 10, the aberrometer 12 and the holder 18 can be moved into the treatment beam path, but alternatively, a pivoting movement may also be provided. FIG. 10 only shows part of the treatment system 46 and, in particular, of the deflecting unit 5. Of the deflecting unit 5, optics 31, 32, 33 and 34 in a housing 35 of the treatment system 1 are shown.

The beam redirecting unit 17 in the aberrometer 12 is provided as a dichroic redirecting mirror, which, due to a suitable coating, is transparent to the optical radiation of the treatment laser beam, but reflects the optical radiation of the measurement ray bundle 15, so that ablation is possible without moving the beam redirecting unit. A possible attenuation of the treatment laser beam 3 by the beam redirecting unit 17 can then be taken into account when determining the actual values of the system parameters from the examination data.

In order to determine the values of the system parameters, the aberrometer 12 with the holder 18 and the calibrating body 11 held therein and optionally mounted is moved or pivoted under the treatment laser beam 3 in a manner defined for ablation. This process is effected manually in this embodiment or automatically in another preferred embodiment of the invention, e.g. by electric motor drives. This arrangement has the advantage that the ablation progress on the calibrating body can be observed at the detecting frequency of the aberrometer.

In sixth and seventh embodiments, the system parameter determining device of the preceding embodiment is modified such that the aberrometer 12 is provided with a different beam redirecting unit 17, which is movable, manually or automatically, in and out of the treatment beam path.

An eighth preferred embodiment of the system parameter determining device differs from the system parameter determining device of the fifth to seventh embodiments by a magazine, in which a plurality of calibrating bodies, optionally mounted, can be stored as a reserve. As the magazine, in particular, a rotatable or pivotable changing revolver may be provided, from which an operator can reload another calibrating body.

A ninth preferred embodiment of the invention differs from the previously described embodiments in that the calibrating body, with a possible mount, is exchangeable via an electrically, preferably automatically, controlled changing device, e.g. with an electric motor drive.

Figure 11:
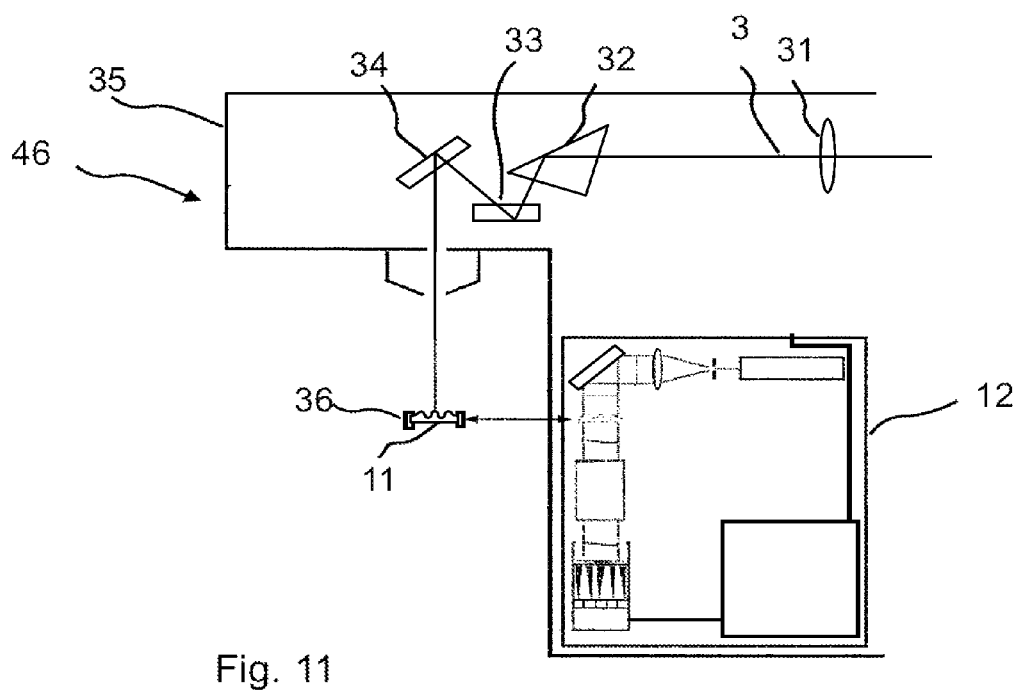
FIG. 11 shows a schematic partial representation of a treatment system comprising a system parameter determining device, which includes a movable holder for a calibrating body, according to a sixth preferred embodiment of the invention.

A tenth preferred embodiment of the invention differs from the fifth preferred embodiment of the invention in that not the entire aberrometer 12 is movable so as to move the calibrating body 11 held therein under the treatment laser beam 3, but only the calibrating body 11 is transferred, in an alternating manner, under the treatment laser beam 3 for ablation, and into the measurement ray bundle 15 of the aberrometer 11 for examination, for example by means of a wavefront measurement. For this purpose, as shown in FIG. 11, a holder 36 for an optionally mounted calibrating body 11 is attached to the system parameter determining device 7 or to the treatment system 46, which holder is movable back and forth, in particular pivotable or displaceable, manually between an ablation position, in which the calibrating body held in the holder 36 is located in the treatment beam path, and a measurement position, in which, for examination, the calibrating body held in the holder 36 is in the examining unit 8, which is the aberrometer 12 in the example, in particular in a measurement beam path. Otherwise, the system parameter determining device does not differ from the system parameter device 7 of the fifth embodiment. The treatment system 46 is unchanged.

In a modification of the tenth embodiment, the holder 36 is movable by a drive, preferably in an electrically controlled manner.

Figure 12:
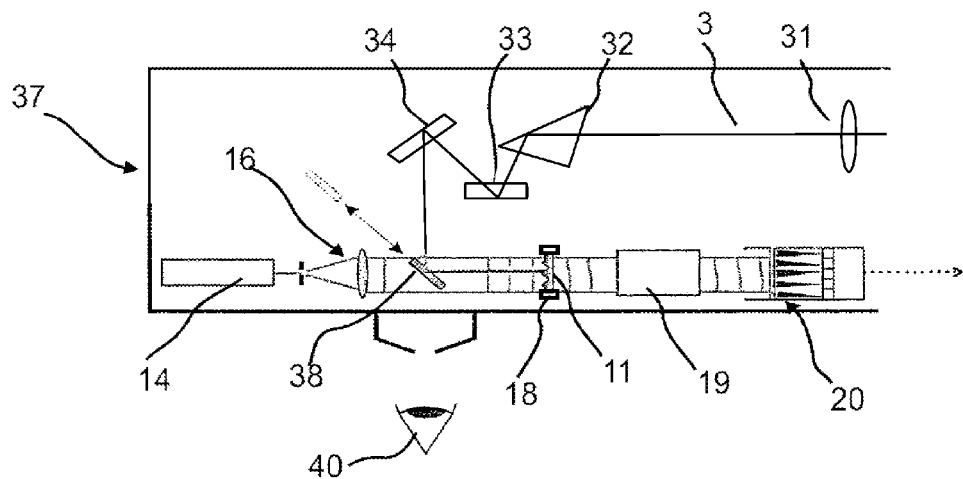
FIG. 12 shows a schematic partial representation of a treatment system comprising a system parameter determining device according to an eleventh preferred embodiment of the invention.

Part of a treatment system 37 comprising an integrated system parameter determining device 39 according to an eleventh preferred embodiment is shown in FIG. 12 and differs from the fifth embodiment in that the treatment laser beam 3 is directable onto a calibrating body 11 via a movable deflecting mirror 38, said calibrating body 11 being held in the system parameter determining device 39. Thus, the holder, or the calibrating body 11, respectively, and the examining unit need not be moved in order to determine system parameters.

The system parameter determining device 39 differs from the system parameter determining device 7 of the fifth embodiment in that the measurement beam path extends linearly. For all components of the system parameter determining device 39, except for the redirecting unit 17, explanations apply accordingly. The treatment system 37 comprises the same components as the treatment system 1, wherein the deflecting unit 5, in particular, is provided as in the fifth embodiment. Therefore, the same reference numerals are used for the same components.

The deflecting mirror 38 is movable between a treatment position, in which it is arranged neither in the treatment beam path nor in the measurement beam path and, thus, allows treatment of an eye 40, and an ablation and measurement position. In the example, the redirecting mirror 38 is linearly displaceable; in other embodiments, it may also be pivotable or rotatable.

In the ablation and measurement position, the deflecting mirror 38 is arranged at the point of intersection of the treatment beam path and the measurement beam path. Due to a suitable coating, it reflects optical radiation of the treatment laser beam 3 and transmits optical radiation of the measurement ray bundle 15, so that the progress of ablation can be detected, during ablation, at the detecting frequency of the aberrometer 12.

Movement of the deflecting mirror 38 between the treatment position and the ablation and measurement position is manually effected in the illustrated embodiment. In a further modification, said movement may be effected by means of a suitable drive. Alternatively, a separate mirror may be used for coupling in the measurement ray bundle, e.g. between the calibrating body and the deflecting mirror 38.

Figure 13:
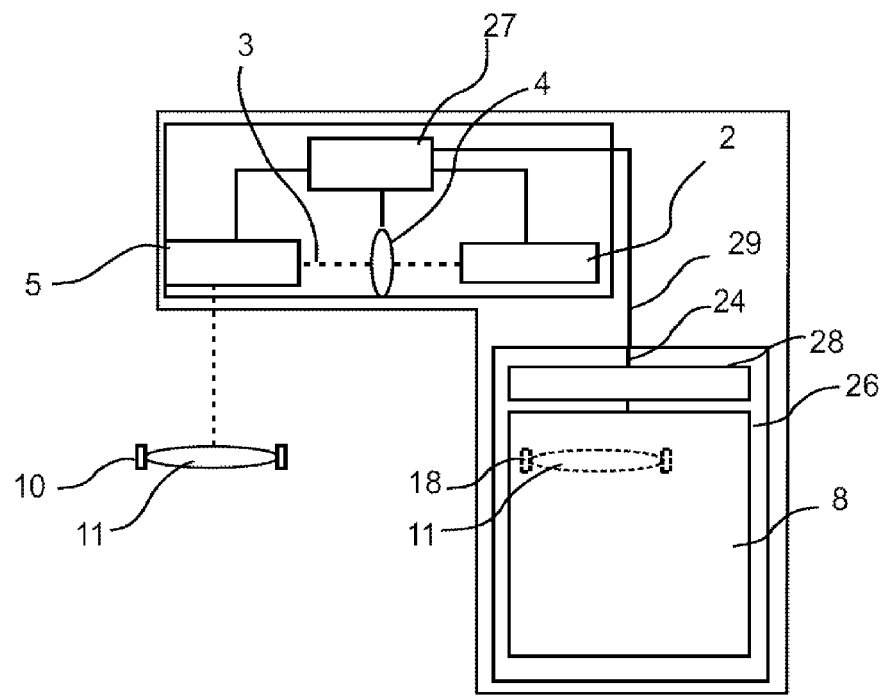
FIG. 13 shows a schematic representation of a treatment system comprising a system parameter determining device according to a twelfth preferred embodiment of the invention.

A twelfth embodiment shown schematically in FIG. 13 differs from the third to eleventh embodiments in that, instead of the control unit 6 and the evaluating unit 9, the control unit 27 and the evaluating unit 28 of the second embodiment are used, which are also connected via a data link 29. Like in the second embodiment, this enables automatic calibration. In this case, too, the evaluating unit may be integrated into the control unit or the measurement data processing unit of the examining unit 8 or of the aberrometer 12, respectively.

Figure 14:
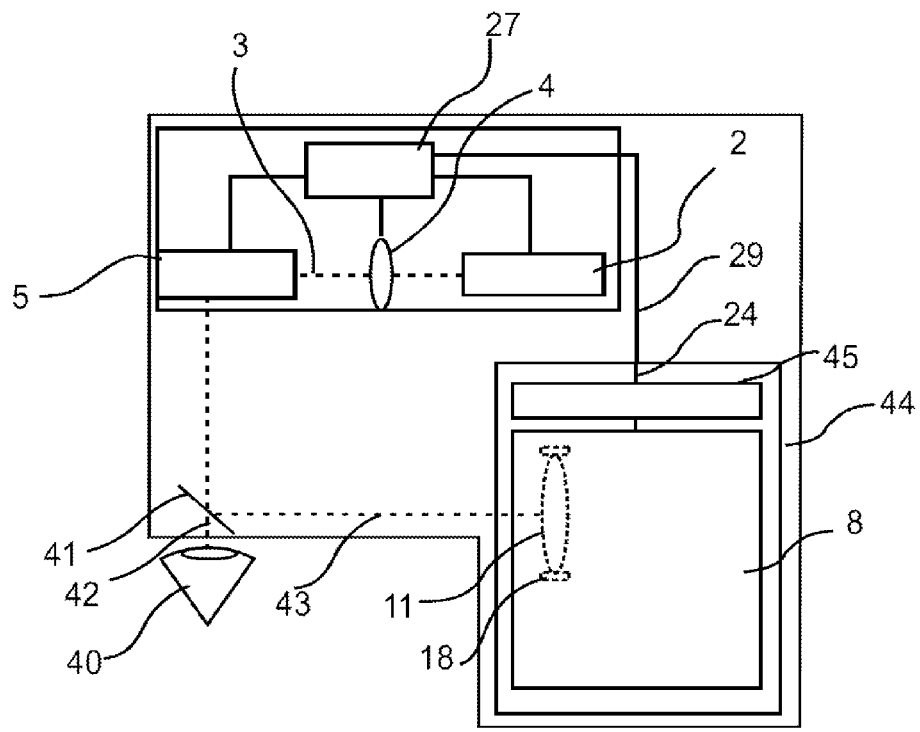
FIG. 14 shows a schematic representation of a treatment system comprising a system parameter determining device according to a thirteenth preferred embodiment of the invention.

A treatment system comprising an integrated system parameter determining device according to a thirteenth embodiment is shown in FIG. 14. It allows measurement, monitoring and control of the ablation during treatment of the eye. In contrast to the twelfth embodiment in FIG. 13, the holder 18 for the calibrating body 11 is not movable. Instead, the treatment laser beam 3 is split into two partial beams by a beam splitter 41, so that one partial beam 42 is used for treatment of the eye and the other partial beam 43 is used for ablation of the calibrating body 11. Except for the beam splitter 41 and optionally the housing, the treatment system corresponds to the treatment system of the twelfth embodiment; likewise, the system parameter determining device 44 corresponds to the system parameter determining device of the twelfth embodiment, except for the holder 18 and the evaluating unit 45. Therefore, identical reference numerals are used for identical components, and the aforementioned explanations for these components also apply here.

The evaluating unit 45 differs from the evaluating unit 28 by two features. On the one hand, when determining the correction values in the evaluating unit 45 or in its correction value determining unit, it takes into consideration that the treatment laser beam 3 is split into the two partial beams. On the other hand, the evaluating unit 45 determines actual values of system parameters from the progress of the ablation. In the treatment and simultaneous determination of actual values of the system parameters, examination data for the calibrating body 11 are detected, e.g. by measurement of the wavefront deformation and evaluation of the data while generating wavefront data, with a predetermined detection frequency of the aberrometer of the twelfth embodiment. From these data, actual values of the system parameters are then determined at the same frequency, which actual values, again at the same frequency, provide correction values of correction parameters, with which the control unit 27 accordingly controls the adjusting units of the treatment system.

Therefore, in the thus cyclic determination of actual values of the system parameters, reference data are determined for the ablation progress which is to be expected on the basis of the ablation profile, which was at least indirectly sensed via the examination data in the preceding cycle, in the presence of the desired values of the system parameters expected during determination of the correction values in the preceding cycle. Actual values of the system parameters in the current cycle are then determined by comparing the examination data in the current cycle with the reference data thus determined by the examination data of the preceding cycle. Therefore, the evaluating unit 45 is provided for cyclic determination of actual values of at least one system parameter or of deviations of at least one system parameter, respectively, as a function of examination data corresponding to an ablation profile determined in a preceding cycle and of examination data of a current cycle.

The thus achieved re-adjustment of system parameters to desired values at the detection frequency of the aberrometer by determining the corresponding actual values or deviations from desired values and, from these, the correction values, as well as the re-adjustment of the corresponding adjusting units during treatment of a patient enable an ablation of the eye which corresponds very precisely to the requirements. Accordingly, fixed ablation programs can be carried out during the entire treatment in the case of constantly optimal system parameters.

As mentioned in the preceding embodiments, the evaluating unit 45 may be integrated, as an alternative, also into the control unit 27 or the measurement data processing unit 13.

Figure 15:
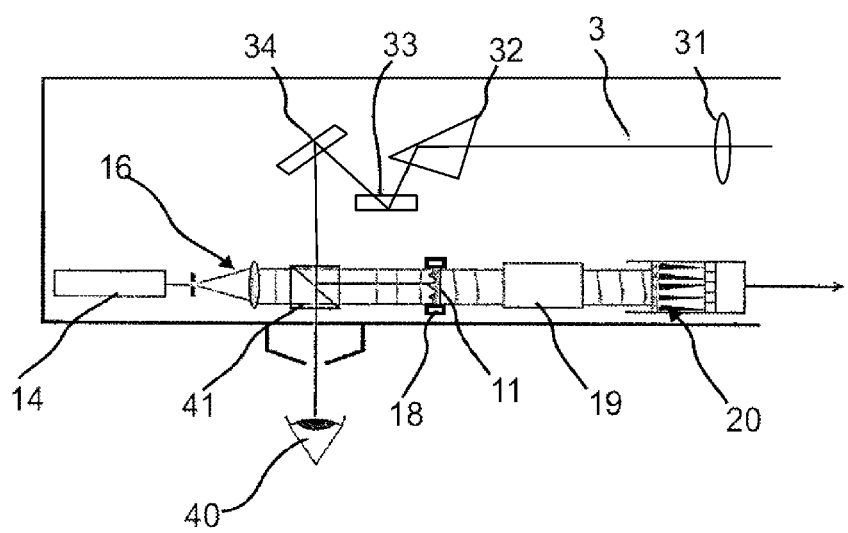
FIG. 15 shows a schematic partial representation of the treatment system comprising the system parameter determining device of FIG. 14.

A more concrete representation of part of a treatment system according to this embodiment may be structured, as shown in FIG. 15, similar to the treatment system 37 of the eleventh embodiment in terms of the beam path. The deflecting mirror 38 is then replaced by the beam splitter 41. The beam splitting may take different values, which are to be determined when determining the system parameters and the correction values, and merely needs to be defined once for a specific arrangement. The entire system for control of the ablation is then designed and calibrated according to this beam splitting ratio.

In a fourteenth embodiment, control of the ablation is effected in a modified form. As compared to the thirteenth embodiment, the control unit 27 and the evaluating unit 45 are modified. As already mentioned, when determining the system parameters during treatment, the ablation progress is determined, at least indirectly, by locally determining the surface profile of the calibrating body over the surface. Description of the surface obtained by ablation is possible via pure elevation data, but also as a polynomial decomposition, e.g. a decomposition into Zernike polynomials. The modified evaluating unit is now adapted such that the achieved actual ablation profile is output, with the correction values, to the modified control unit. The latter not only re-adjusts the adjusting units in accordance with the correction values, as in the preceding embodiment, but also carries out a comparison of the actual ablation profile with the desired ablation profile of the calibrating body to be achieved by the treatment, which desired ablation profile was defined before treatment and was determined from the desired ablation profile of the eye. On the basis of the re-adjusted adjusting units and, thus, system parameters, the ablation program is now modified by means of a suitable program module such that the actual ablation of the calibrating body 11 approaches the desired ablation of the calibrating body 11 as far as possible.

If, for example, a reliable relation has been established, by suitable empirical examinations, between the ablation behavior of the eye or of the cornea and that of the calibrating body, a desired desired ablation profile of the eye can thus be achieved very precisely and quickly.

This embodiment no longer requires ablation using predetermined ablation programs or algorithms based on values gained by experience for ablation, as was previously the case, with a predetermined ablation program. Rather, control of the ablation program is effected dynamically and on the basis of the currently determined actual ablation of the calibrating body. Thus, ablation may be effected at those locations of the cornea, where no optimal target or desired surface has been achieved yet.

The invention claimed is:

1. A method for determining an actual value of at least one laser system parameter or a deviation from a desired value of the at least one laser system parameter of an eye treatment system emitting a treatment laser beam, the method comprising:

ablating a surface of a calibrating body alternately or simultaneously with ablating a surface of an eye by at least one partial beam of the treatment laser beam according to a predetermined ablation program the ablating resulting in an ablated surface of the calibrating body;

examining the ablated surface of the calibrating body ablated with the treatment laser beam with at least one of aberrometry or profilometry to obtain examination data; and using the examination data to determine an actual value of the at least one laser system parameter or a deviation from a desired value of the at least one laser system parameter and to adjust the at least one laser system parameter during ablating of the surface of the calibrating body and the surface of the eye.

2. The method of claim 1, further comprising selecting said calibrating body to be plate-shaped in an area to be ablated.

3. The method of claim 1, further comprising selecting said calibrating body to be spherically-shaped in an area to be ablated.

4. The method of claim 1, further comprising selecting said calibrating surface comprises a shape of a corneal portion of an eye to be treated.

5. The method of claim 1, further comprising selecting said calibrating body to be polymethylmethacrylate.

6. The method of claim 1, wherein said calibrating body is non-transmitting for a wavelength of optical radiation used for measurement during said examination.

7. The method of claim 1, further comprising separating said treatment laser beam from optical radiation used for examination.

8. The method of claim 7, wherein the separating is performed using a filter.

9. The method of claim 1, further comprising arranging said calibrating body in a working plane of the eye treatment system during examination.

10. The method of claim 1, further comprising splitting said treatment laser beam and ablating said calibrating body with a first beam portion and treating the eye with another beam portion.

11. The method of claim 1, further comprising providing a measurement ray bundle to examine said calibrating body and coupling said measurement ray bundle colinearly to at least one of said partial beams to ablate said calibrating body.

12. The method of claim 1, further comprising modifying a wavefront to examine an ablation condition of said ablated surface with aberrometry.

13. The method of claim 1, further comprising evaluating wavefront data relating to a wavefront to examine an ablation condition of said calibrating body with aberrometry.

14. The method of claim 1, further comprising performing said profilometry using an optically operating method.

15. The method of claim 1, further comprising determining said actual value or deviation from the desired value from the examination data for at least two system parameters.

16. The method of claim 1, further comprising comparing examination data with corresponding reference data.

17. The method of claim 1, further comprising examining a reference body having a predetermined ablation pattern by at least one of aberrometry or profilometry and using said examination data as reference data.

18. The method of claim 1, wherein the method is carried out in a cyclic manner, further comprising determining reference data for a current cycle of ablating the surface of the calibrating body using examination data of a preceding cycle.

19. The method of claim 1, further comprising determining at least one correction parameter value as a function of at least one of said determined actual value or deviation from the desired value, said correction parameter value usable to reduce at least one deviation from a desired condition.

20. The method of claim 1, further comprising modifying at least one corresponding setting of an adjusting unit of the treatment system as a function of at least one of the determined actual value or deviation from the desired value to reduce deviations from a desired condition or function.

21. The method of claim 1, further comprising modifying at least one of a position or an intensity of said treatment laser beam over time to achieve a predetermined ablation profile according to at least one of the determined actual value or deviation from the desired value.

22. The method of claim 1, further comprising modifying at least one of a position or an intensity of the treatment laser beam over time to achieve at least one parameter value for a program according to at least one of the determined actual value or the deviation from the desired value.

23. The method of claim 1, further comprising automatically changing a setting of the treatment system using at least one of the determined actual value or deviation from the desired value to reduce the deviation between actual value and desired values.

24. The method of claim 1, further comprising selecting the system parameter from the group consisting of:
at least one of centration or position of the deflecting unit relative to a system for tracking eye movements;
at least one of the mean total fluence, energy, or power of the treatment laser beam;
a half-width of the treatment laser beam;
information about a spot shape of the treatment laser beam;
an energy distribution in a treatment spot;
characteristics of a transition zone between optically active and inactive ablation zones and their relation to beam parameters;
at least one of a short-term and long-term stability of or fluctuations in total fluence, total energy, or total power of the treatment laser beam;
short-term and long-term drift in the deflecting unit;
deviations from an optimal working distance;
an efficiency of suction or removal of fumes generated by ablated material during ablation;
temperature stability; and
a dependence of the system parameters on other ambient parameters.

25. A system parameter determining device for determining at least one actual value of a laser system parameter or a deviation from a desired value of at least one laser system parameter of a system for treatment of an eye by a treatment laser beam emitted by said system, the device comprising:
an examining unit that examines at least one portion of an ablated surface of an ablated calibrating body by at least one of aberrometry or profilometry, the ablated calibrating body being subject to ablation alternately or simultaneously with the eye; and
an evaluating unit operably coupled to the examining unit to determine an actual value of the system parameter or a deviation from the desired value of the system parameter with examination data determined during examination of the ablated calibrating body and operably coupled to the system for treatment of an eye by a treatment laser beam to return feedback information to the system for treatment of an eye by a treatment laser beam regarding the at least one laser system parameter during ablating of the surface of the calibrating body and the surface of the eye.

26. The device of claim 25, further comprising a filter and a photo detector, wherein said filter is selectively arranged to precede said photo detector in a beam path of said treatment laser beam, wherein said filter does not transmit optical radiation having a polarization or a wavelength of said treatment laser beam.

27. The device of claim 25, wherein said examining unit comprises an aberrometer.

28. The device of claim 25, wherein said aberrometer comprises a Hartmann-Shack sensor.

29. The device of claim 25, wherein said examining unit comprises an optically operating profilometer.

30. The device of claim 25, wherein said evaluating unit is configured to determine at least one of said actual value or deviation from a corresponding desired value from examination data for at least two system parameters.

31. The device of claim 25, wherein said evaluating unit is configured to determine the deviation from the desired value by comparing said examination data with corresponding reference data.

32. The device of claim 31, further comprising a memory for storing said reference data.

33. The device of claim 31, further comprising a reference body having a predetermined reference ablation pattern already applied thereto.

34. The device of claim 31, wherein said evaluating unit is configured to determine reference data during cyclic detection of examination data for a current cycle of ablating the surface of the calibrating body from examination data of a preceding cycle.

35. The device of claim 25, further comprising a correction value determining device to determine at least one correction parameter value of the treatment system as a function of at least one of the determined actual value or deviation from the desired value to reduce the deviation between the actual value and desired value.

36. The device of claim 25, wherein the system parameter is selected from the group consisting of:
- at least one of centration or position of the deflecting unit relative to a system for tracking eye movements;
- at least one of the mean total fluence, energy, or power of the treatment laser beam;
- a half-width of the treatment laser beam;
- information about a spot shape of the treatment laser beam;
- an energy distribution in a treatment spot;
- characteristics of a transition zone between optically active and inactive ablation zones and their relation to beam parameters;
- at least one of a short-term and long-term stability of or fluctuations in total fluence, total energy, or total power of the treatment laser beam;
- short-term and long-term drift in the deflecting unit;
- deviations from an optimal working distance;
- an efficiency of suction or removal of fumes generated by ablated material during ablation;
- temperature stability; and
- a dependence of the system parameters on other ambient parameters.

* * * * *

UNITED STATES PATENT AND TRADEMARK OFFICE
CERTIFICATE OF CORRECTION

| | |
|---|---|
| PATENT NO. | : 8,303,577 B2 |
| APPLICATION NO. | : 10/565511 |
| DATED | : November 6, 2012 |
| INVENTOR(S) | : Manfred Dick et al. |

Page 1 of 1

It is certified that error appears in the above-identified patent and that said Letters Patent is hereby corrected as shown below:

Column 1, line 55:
".... sphero-cyiindricai corrections ..." should be -- ... sphero-cylindrical corrections ... --

Column 14, line 67:
"... the treatment, laser beam emitted ..." should be -- ... the treatment laser beam emitted ... --

Column 26, line 44:
"... a desired desired ablation profile ..." should be -- ... a desired ablation profile ... --

Column 28, line 46:
" ...unit that examines_at least one portion" should be -- ... unit that examines at least one portion ... --

Signed and Sealed this
Fifth Day of February, 2013

Teresa Stanek Rea
*Acting Director of the United States Patent and Trademark Office*